US009816376B2

(12) United States Patent
Pope et al.

(10) Patent No.: US 9,816,376 B2
(45) Date of Patent: Nov. 14, 2017

(54) IN SITU EVALUATION OF UNCONVENTIONAL NATURAL GAS RESERVOIRS

(71) Applicant: Gas Sensing Technology Corp, Laramie, WY (US)

(72) Inventors: John Pope, Laramie, WY (US); Quentin Morgan, Murarrie (AU)

(73) Assignee: Gas Sensing Technology Corp., Laramie, WY (US)

( * ) Notice: Subject to any disclaimer, the term of this patent is extended or adjusted under 35 U.S.C. 154(b) by 272 days.

(21) Appl. No.: 14/254,079

(22) Filed: Apr. 16, 2014

(65) Prior Publication Data

US 2014/0300895 A1 Oct. 9, 2014

Related U.S. Application Data

(60) Continuation of application No. 14/250,552, filed on Apr. 11, 2014, which is a division of application No. 13/545,334, filed on Jul. 10, 2012, now Pat. No. 8,760,657.

(60) Provisional application No. 61/928,563, filed on Jan. 17, 2014, provisional application No. 61/937,757, filed on Feb. 10, 2014, provisional application No. 61/602,939, filed on Feb. 24, 2012.

(51) Int. Cl.
*G01N 21/00* (2006.01)
*E21B 47/00* (2012.01)
(Continued)

(52) U.S. Cl.
CPC .......... *E21B 49/088* (2013.01); *E21B 47/10* (2013.01); *E21B 47/102* (2013.01); *E21B 49/00* (2013.01);
(Continued)

(58) Field of Classification Search
CPC ...... E21B 49/088; E21B 47/102; E21B 49/00; E21B 47/10; E21B 49/08; E21B 49/087; G01V 8/02; G01N 21/65
(Continued)

(56) References Cited

U.S. PATENT DOCUMENTS

| 4,456,069 A * | 6/1984 | Vigneri | E21B 36/00 |
| | | | 166/303 |
| 5,225,674 A * | 7/1993 | Frantz | G01V 5/06 |
| | | | 250/259 |

(Continued)

OTHER PUBLICATIONS

A.R. Smith, et al., "In-Situ Optical Fluid Analysis as an Aid to Wireline Formation Sampling", SPE Formation Evaluation, Jun. 1995, pp. 91-95.

*Primary Examiner* — Ovidio Escalante
(74) *Attorney, Agent, or Firm* — Adolph Locklar

(57) ABSTRACT

An analytical method that establishes a thermodynamic equilibrium or known dynamic relationship between the concentrations of gases, natural gas liquids and oils or pressures of gasses in an isolated zone of a shale, or group of distinct shale gas intervals, with the concentrations of fluids or pressures of gasses in a wellbore penetrating the shale interval or intervals. An analytical method for identifying the chemical composition of gas, natural gas liquids and oils and determining their origin in an isolated zone of a shale, or group of distinct shale gas intervals with the identification of chemical composition of gas, natural gas liquids and oils in a wellbore penetrating the shale interval or intervals. A surface measurement apparatus capable of performing the measurement ex-situ. A downhole measurement apparatus capable of reliably performing the measurement in-situ and a downhole straddle-packer assembly capable of isolating part of, or an entire shale interval.

32 Claims, 11 Drawing Sheets

(51) Int. Cl.
*G01V 8/00* (2006.01)
*E21B 49/08* (2006.01)
*E21B 47/10* (2012.01)
*G01V 8/02* (2006.01)
*E21B 49/00* (2006.01)
*G01N 21/65* (2006.01)

(52) U.S. Cl.
CPC ............ *E21B 49/08* (2013.01); *E21B 49/087* (2013.01); *G01N 21/65* (2013.01); *G01V 8/02* (2013.01)

(58) Field of Classification Search
USPC ........ 356/300–301, 317, 326, 432–437, 319; 250/269.1, 339.11, 341.8, 256; 73/152.19, 152.31, 152.24, 152.28; 166/95.1, 97.1, 308.1, 387, 191, 250.01
See application file for complete search history.

(56) References Cited

U.S. PATENT DOCUMENTS

| | | | |
|---|---|---|---|
| 5,285,388 A * | 2/1994 | McCoy et al. | 702/12 |
| 5,494,108 A | 2/1996 | Palmer et al. | |
| 6,147,496 A * | 11/2000 | Strack | G01V 3/28 324/343 |
| 6,254,828 B1 * | 7/2001 | LaCount | G01N 21/3504 250/343 |
| 6,678,050 B2 | 1/2004 | Pope | |
| 7,216,702 B2 | 5/2007 | Carlson | |
| 7,511,819 B2 * | 3/2009 | DiFoggio | 356/436 |
| 7,821,635 B2 | 10/2010 | Pope | |
| RE44,728 E | 1/2014 | Pope | |
| 8,640,771 B2 | 2/2014 | Pope | |
| 2002/0003115 A1 * | 1/2002 | Conaway | B03B 9/02 210/759 |
| 2003/0048450 A1 * | 3/2003 | Pope | G01J 3/28 356/435 |
| 2003/0080604 A1 * | 5/2003 | Vinegar | E21B 43/243 299/14 |
| 2006/0157242 A1 * | 7/2006 | Graham | E21B 43/305 166/268 |
| 2007/0012434 A1 * | 1/2007 | Ringgenberg et al. | 166/66 |
| 2007/0137293 A1 * | 6/2007 | Pop | E21B 49/005 73/152.23 |
| 2008/0111064 A1 * | 5/2008 | Andrews et al. | 250/269.1 |
| 2012/0227960 A1 * | 9/2012 | Pope et al. | 166/250.01 |

\* cited by examiner

IN SITU EVALUATION OF UNCONVENTIONAL NATURAL GAS RESERVOIRS

RELATED DISCLOSURES

This disclosure is a CONTINUATION IN PART of application Ser. No. 14/250,552 entitled "In-Situ Detection and Analysis of Methane in Coal Bed Methane Formations with Spectrometers" filed Apr. 11, 2014 and which is a Divisional application of Ser. No. 13/545,334 also entitled "In-Situ Detection and Analysis of Methane in Coal Bed Methane Formations with Spectrometers" filed Jul. 10, 2012, and further claiming the benefit of and priority to provisional application 61/609,939 filed Feb. 24, 2012. This disclosure claims the benefit of and priority to Provisional Application No. 61/928,563 entitled In Situ Evaluation of Unconventional Natural Gas Reservoirs filed Apr. 16, 2013, and Provisional Application No. 61/937,757 also entitled In Situ Evaluation of Unconventional Natural Gas Reservoirs filed Jul. 18, 2013. Said applications are incorporated herein by reference in their entirety.

BACKGROUND OF INVENTION

Technical Field

This disclosure is directed to a sensor and to a sensing method that identifies the chemical composition of gases, such as solubilized and free gas, and liquids, such as natural gas liquids, water and oil, in unconventional oil and gas shale reservoirs, measures the concentrations of key constituents present in the gases and liquids, determine the partial pressure of each gas species, and equates the various measurements to shale reservoir production factors. Specifically, the disclosed sensor and sensing methods establishes a constant relationship between a gas pressure or composition of gases and liquids in a wellbore and a gas pressure or composition of fluids, comprising gases and liquids, in a far-acting reservoir and then measures these variables in the wellbore using one or more sensors in the wellbore.

Alternately, the disclosed sensor and sensing method establishes a dynamic relationship of known quality between a gas pressure or composition of gases and liquids in a wellbore and a gas pressure or composition of fluids, comprising gases and liquids, in a far-acting reservoir and then measures temporal conditions reflecting that dynamic relationship and uses the known quality to calculate a gas equilibrium reservoir pressure.

Alternately, the disclosed sensor and sensing method establishes a relationship between the temporal changes in depth of chemical transitions within a fluid column in a wellbore to the origin of each chemical in one or more shale intervals penetrated by the well.

Methods and apparatus suitable for quickly establishing communication between the wellbore and reservoir are disclosed, as are methods and apparatus for distinguishing between multiple gas and liquid chemical types that may be present in the reservoir, and their origin within a specific reservoir or group of reservoirs.

The disclosure provides a new reservoir evaluation technology that allows operators to high grade prospective oil and gas shales and target pay zones, allowing operators to avoid non-economic completion costs and water use. By providing an invention that can be used to quickly, accurately and inexpensively assess oil and gas shale resources at a high data density, this disclosure enables more complete evaluation of oil and gas shale resources. This evaluation focuses operators on developing completion methods for oil and gas shale targets that warrant investment, reduce overall water usage, and increase the conversion of shale resources into shale reserves. In this application, the term shale refers to a class of unconventional oil and gas resource rocks that includes shales, clays, tight sands, mudstones, and tight carbonates. The invention removes uncertainty regarding estimates of gas-in-place, liquids-in-place, estimated ultimate recovery, and production potential, incenting more rapid capital investment by shale operators and investors, and accelerating hydrocarbon production from these reservoirs. This invention enables shale operators to increase exploration success rates, reduce finding costs, reduce completion costs, and reduce environmental impacts without constraining production.

Determination of Oil and Gas Shale Production Factors

This invention also relates to a method and system of determining gas content, dewatering time, critical desorption pressure, gas-oil ratio, gas-liquid ratio, ratios of gas and oil to water, estimated ultimate recovery, and/or other reservoir and operational variables, referred to as production factors, for shale wells, wherein the hydrocarbon is at least partially dissolved in water within the reservoir. In particular, this invention relates to a method and system for measuring a partial pressure of methane and other higher hydrocarbon gases or a predictor substance for a shale gas and liquid reservoir and determining production factors therefrom.

Apparatus and Method of Combining Zonal Isolation and In Situ Spectroscopic Analysis of Reservoir Fluids for Shale Reservoirs This invention also relates methods and apparatus that enable active isolation and analysis of shale reservoirs. Testing multiple shale reservoirs situated at various depths in the same well is difficult due to commingling of the fluids from the shale reservoirs that enter the wellbore. As a result, fluids in such multi-zone wellbores may originate from more than one shale reservoir, or only one shale reservoir, depending on relative shale reservoir pressures, and analysis of such fluids cannot readily be attributed to a particular reservoir under static conditions.

This invention allows ready attribution of fluid properties to the correct shale reservoir by actively isolating part of or a whole shale in a wellbore, flowing fluid from the isolated interval, analyzing such fluid, and thereby analyzing the production factors of interest in that particular shale.

The invention also relates the apparatus that can be used in this method. This apparatus includes isolating the shale intervals by using existing casing, by setting bridge plugs and retrievable bridge plugs, by using pack-off technologies, and/or by using active pumping to favor production of water or oil from a particular shale interval.

The invention also describes use of a downhole spectroscopic analyzer, a surface spectroscopic analyzer that is coupled to the flowback fluid tubing from the wellbore, and a surface spectroscopic analyzer that is coupled to a downhole sensor analysis chamber using optical fibers with the shale isolation apparatus.

BACKGROUND

Shale gas and liquids, where gas refers to solubilized and free gas, and liquids refers to natural gas liquids, such as ethane, propane, butane, and also to water and oil, represent the most secure method for the United States to satisfy its current and future hydrocarbon needs. Those needs are driven primarily by U.S. demand for electricity generation (2009 *Annual Energy Outlook*, Energy Information Administration). A failure to meet those needs with domestic production will result in decreased availability of electricity in the U.S., increased imports of LNG and oil bringing reduced national security, or both.

However, due to the high completion costs associated with shale gas and liquid wells, continued growth in development remains highly sensitive to natural gas and oil prices. In addition, substantial growth in shale gas and liquids development will require significant additional water resources to be used during completion. Either of these issues could limit growth in shale gas and liquids production and reduce U.S. energy security.

Domestic electricity demand continues to drive high growth in demand for natural gas. Conventional sources of natural gas are in decline. Increased production from unconventional sources, particularly coalbed methane, tight sands and shale gas, are required not only to meet future growth in demand, but to meet existing demand as well. In fact, by 2030, the Energy Information Administration predicts that unconventional sources of natural gas will contribute more to U.S. production than conventional ones (2009 *Annual Energy Outlook*).

Of the available unconventional sources of natural gas, tight sands, coalbed methane and shale gas has received the most significant operator interest. However, like most unconventional natural gas resources, exploration of gas and liquids in shales has a long history, even predating the first oil well. Commercial gas production was achieved from the 1970s to 1999 in the Ohio, Antrim, Barnett, and Lewis shales. However, development of new hydraulic fracturing techniques that allowed greater recovery rates in the Barnett shales led to a rapid increase of gas production in that basin and a belief that successful development could occur in other, previously ignored basins (Reimers, IHS Energy, 2008).

Broad application of those fracturing techniques, along with directional drilling of lateral wellbores, to shale intervals has resulted in a sudden surge in shale gas exploration and production. In 1999, natural gas production from shale intervals was about 0.4 Tcf, or 2% of U.S. production. By 2006, natural gas production from shale intervals was about 1.1 Tcf, or 5.5% of U.S. production (Figures from paper presented by Curtis, Hill and Lillis at *NAPE* 2008). The potential exists for significant further growth in shale gas production: only a few percent of the 600+Tcf of U.S. lower-48 shale gas reserves has been produced to date (Curtis, Hill, Lillis, ibid).

The comparative nascent state of U.S. shale oil production contrasts sharply with its rapid pace of growth. When significant shale oil drilling activity first began in 2007 across the U.S. portion of the Bakken formation (North Dakota and Montana), the resource potential of tight and shale oil was virtually absent from the United States and the international oil map. It remained so until 2011, when Bakken shale oil production started to surprise most experts and the Eagle Ford and Permian Basin shale formations began to emerge as additional contributors to the unexpected shale oil boom. By the end of 2012, that boom released an overall production of more than 1.5 mbd of crude oil, starting from virtually zero in 2006, with Bakken now estimated to hold 900 billion barrels OOP. That would make Bakken's endowment alone larger than Saudi Arabia. (Maugeri, *The Shale Oil Boom: A U.S. Phenomenon*).

One of the fundamental challenges associated with producing gas and liquids from complex formations like coals and shale intervals is that the depositional processes that created the rock, and the biogenic and thermogenic processes that reformed portions of that rock into gas, were by nature heterogeneous. These heterogeneities in deposition and oil and gas evolution were compounded by the naturally heterogeneous processes of faulting, uplift and fracturing that the formations have undergone since deposition. As a result, the shale reservoirs being developed can have significant heterogeneity in hydrocarbon accumulation volumes, in the types and composition of hydrocarbons, and in the fracture networks they contain.

These factors have led to the conventional wisdom that development of every shale target requires development of new completion and production techniques. In the shale industry, these factors are slowly leading to a realization that reservoir heterogeneity is much higher than originally thought and affects production success more broadly than had been hoped.

The primary challenge facing shale gas and liquid operators relates to the tightness of most formations. Shale intervals are low porosity rocks intersected in many cases by extensive fracture networks. Because shale intervals typically are not saturated with water, many of the fractures contain gas and liquids (typically methane as the predominant hydrocarbon). In fact, 30% or more of the gas in a shale may be compressed into its fracture network.

However, most of the gas and liquid in a shale is located in the nanopores that permeate the rock or is associated with kerogen and other constituents. Unfortunately, effective permeability of the shale is low, and pore-trapped gas and liquids typically cannot be produced at rates that are economic. Gaining economic access to those hydrocarbons is therefore achieved by taking advantage of natural fracture networks within the shale interval, or more typically, by creating macro and micro transport pathways, such as induced fracture networks and lateral wellbores.

Fracturing shale intervals and drilling lateral wellbores is expensive. Shale intervals typically present an enormous number of possible completion targets. With gross packages ranging from 10 feet to 3000 feet thick, shale intervals present an unusual challenge in selecting completion targets for operators.

In addition, not all oil and gas shale contains economic amounts of hydrocarbons. As a result, some of these completion costs are ultimately wasted on non-productive or non-economic targets. For example, one study measured methane gas contents ranging from 7.9 scf/ton to 190 scf/ton in the same shale gas wells (Triangle Petroleum press release, Jan. 30, 2008); a recent review pointed to variations from 40 to 100 scf/ton and 150 to 350 scf/ton of methane gas in other shale formations (Jenkins, Boyer, SPE JPT, paper 103514, February 2008). Furthermore, the extremely low porosity of oil shale intervals, the dramatic decline rates after the early months of production of each shale well and its relatively high overall costs further marginalize economic development of this resource, and have contributed to a widespread belief that recoverable shale oil reserves only represent a tiny fraction (<2 percent) of the original OOP.

Types of gas and liquids available from shale intervals also vary, with some shale intervals providing nearly pure methane and other shale intervals providing appreciable levels of natural gas liquids, and others yielding oil. As those types of fluids have different market demand, operators need a way to discriminate between areas of differing fluid types in order to strategically focus their production on the most needed resources.

As a result, more extensive evaluation of reservoir heterogeneity can enable operators to focus on zones with more of the types of producible hydrocarbon (i.e. a more extensive fracture network or more of a particular type of hydrocarbon) or on zones with enough gas- and liquids-in-place to warrant extensive completion development efforts.

In the case of validating gas- and liquids-in-place levels, this requires evaluation of the gas and liquid content of the shale. Current reservoir evaluation technologies, such as gas and liquid desorption from core sampling, are expensive and slow, and not well-suited to the particular formats in which gas or liquids and rock samples are encountered in shales, causing significant inaccuracies in the results (Hartman, Lasswell, Bhatta, paper presented at 2008 *AAPG Annual Convention*). Other techniques, such as seismic imaging and total organic carbon content can reveal structural or geological characteristics of the reservoir but do not directly analyze gas or liquids.

In the case of coalbed methane formations that are immersed in water and under-saturated in gas, an existing downhole Raman spectrometer (U.S. Pat. No. 7,821,635 which is incorporated by reference herein in its entirety) is capable of measuring solution gas levels and thereby inferring the partial pressure and hydrocarbon gas and natural gas liquids content of the formation. That technology is extensible to measuring solubilized gas concentrations and gas and liquids composition in shale intervals. The potential impact of in-situ Raman spectroscopy technology is immense. To date, shale gas exploration has focused on methane production from intervals oversaturated in gas or significantly under-saturated in water, with success rates similar to the early fairway developments in coalbed methane.

As gas supply from such sources became overly abundant focus shifted to development of natural gas liquids from water saturated and gas under-saturated shale intervals and oil from oil shales. Furthermore, as exploration extends into more complex and marginal frontier and less mature basins, and as new operators enter the industry, exploration success rates will decline. Consequently, without an effective reservoir evaluation technology to pinpoint locations of natural gas liquids, map variations in gas contents, oil-in-place and other production factors, industry will likely encounter development failure rates of 30-60%, similar to current coalbed methane exploration. With an effective reservoir evaluation technology, industry should be able to reduce failure rates to 10-20%, similar to conventional gas exploration, accelerating development of productive shale gas and liquids targets and accelerating overall shale gas and liquids production.

Likewise, significant environmental benefit can be realized through an effective reservoir evaluation technology. Again for shale intervals alone, completing a shale well requires extensive fracturing of the shale in order to better access the gas and liquids trapped in its pores and to increase well production rates to economic levels. This induced fracturing requires large volumes of water; in some wells in the Barnett shale, more than 3.5 million gallons of water are used to complete or re-fracture each horizontal well. More than 4,000 shale gas wells are being drilled in the U.S. each year. If each well uses only 1 million gallons of water for fracturing, the amount of water used annually by the shale gas industry is on the order of 1 billion gallons. Eventually, this water use will result in constriction of the industry's growth due to conflicts with other water users. By deliberately selecting high priority completion targets based on gas and liquids distribution, the industry can likely reduce its water usage by 30-50%, saving 300-500 million gallons of water per year and extending its ability to grow by years if not decades.

Traditionally, shale production factors have been determined by a variety of methods. One method involves retrieval of a core sample of the shale, transportation of the core sample to a laboratory setting, and quantification of the amount of gas contained within the sample shale via gas desorption. This quantity is then analyzed to determine the shale gas content and compared to an adsorption isotherm of the same, or a similar shale in order to determine the relative amounts of free and adsorbed gas and the critical desorption pressure of the adsorbed phase, in order to estimate the ultimate recovery of gas or liquids from the shale. As mentioned previously however, this process is expensive, very time consuming, and error-prone.

Those skilled in the art will recognize that reference to a partial pressure of gas dissolved in a fluid is related to the amount of that gas dissolved in that fluid and that would be in equilibrium with a vapor phase in contact with that fluid. Use of the term "partial pressure of gas in fluid" is meant to encompass, but not be limited to, related terms such as concentration, effective density, quantity, potential volume, potential pressure, and amount.

An aspect of certain preferred embodiments of the invention provides that a production factor such as adsorbed gas content, dewatering time, critical desorption pressure, and/or other reservoir and operational variables can be determined via identification of chemical composition of fluids within a gas under-saturated shale and measurement or determination of the partial pressures of methane and other gases, including natural gas liquids.

In other embodiments, the invention allows locations of natural gas liquids content to be determined in all shale types by chemical fingerprinting, which involves the ability to detect and identify individual chemical species within the reservoir fluid or wellbore headspace. In another embodiment, this same finger printing technique is used to determine oil-gas ratio, gas-liquids ratio and other similar fluid ratios to water.

The critical desorption pressure of adsorbed gases in a gas under-saturated shale reservoir is equal to the partial pressure of those gases in the shale reservoir. By determining the effective partial pressure of adsorbed gases, including natural gas liquids, in a gas under-saturated shale reservoir, extracted reservoir fluid or well fluid, the associated critical desorption pressures may be determined. If the system is in physical and chemical equilibrium the partial pressures of gases in the gas under-saturated shale reservoir, reservoir fluid and well fluid are all equal. However, in practice this is not always the case as many variables may affect the partial pressures and their interrelation to one another. In such cases other measurements or determinations may be used to correlate the partial pressures.

Other production factors applicable to all shale types may be determined utilizing the chemical composition of gases and liquids, movements in transitions between different mixtures of gases and liquids in the wellbore over time, and partial pressure of gases via correlation, modeling, calculation, and other sensor data.

The measurement of the partial pressure for a particular gas can be accomplished via measurement of the dissolved gas concentration in water extracted from the shale into the wellbore. Preferably, the measurement of the concentration is done at a depth of the shale and as near to the shale as possible so that other variables and effects are lessened. This concentration is then correlated to a partial pressure of that gas in the well fluid, and thus shale reservoir. The partial pressure of the gas within an gas under-saturated shale reservoir is then used to determine the gas critical desorption pressure along with an adsorbed gas content of the shale reservoir, dewatering time and other reservoir and operational variables.

The measurement or determination of the partial pressure may also be accomplished in other ways such as by direct measurement of the partial pressure via instrumentation or another variable which correlates to the partial pressure of the gas.

In a preferred embodiment, the concentration of gases dissolved in shale reservoir fluid is measured at a depth in the well at or near the shale of interest. This concentration is then correlated to the partial pressures of those other gases in the fluid. The partial pressures of gases in the fluid are then correlated to the partial pressure of each gas in the reservoir, which equates to their critical desorption pressure in a gas under-saturated shale and is related to the estimated ultimate recovery of each gas.

In certain preferred embodiments of the invention a method for determining a production factor or methane gas content of a gas under-saturated shale is achieved by direct measurement of methane concentration of the wellbore fluid. This measurement in combination with a known or determined solubility property for methane in water allows the calculation of the partial pressure of methane in the wellbore fluid.

If the fluid in the wellbore is in equilibrium with the reservoir fluid, which in turn is in equilibrium with the shale itself, the hydrologic and physical connection between these fluids and the shale allows that the measurement partial pressures of solubilized gases in one fluid to be correlated into a measurement of the other two. The partial pressure of solubilized gases in the fluids is controlled by the amount of each gas present in the shale. More simply stated; when more methane is present in a particular shale, the partial pressure of methane in the fluids is higher.

The methane partial pressure in a gas under-saturated shale is the methane critical desorption pressure, which is the methane saturation point of the shale at that pressure. Dewatering of the well acts to lower the total fluid pressure to a value at or below the critical desorption pressure, which causes devolution of methane out of the shale as free gas, initially from natural or induced fractures if present.

Having determined the methane critical desorption pressure, by further utilizing a methane isotherm of the interested shale, calculations can be made to determine the methane gas content of the gas under-saturated shale and estimate the total methane reserves. As well, the critical desorption pressure can be compared to the rate of decrease of the total reservoir pressure during dewatering, the rate of flow of water from the shale, and other reservoir and operational variables, in order to predict dewatering time and other production factors.

The concentration of methane, other gas, natural gas liquids and oils may be measured by optical spectrometers, membrane-covered semiconductor sensors, mass spectrometers or the like. These concentration measurements can in turn be used to determine gas-oil ratio, gas-liquids ratio and other similar fluid ratios to water.

The concentrations of solubilized gasses which are measured may be directly correlated to a partial pressure for each gas species in the reservoir or any intermediate quantity that is relatable to the amount of each gas in the fluid or parts of the fluid. Each shale interval has unique properties which may affect the correlations. By using an intermediate correlation these properties may be used to enhance the accuracy and precision of the partial pressure determination of each gas in the reservoir.

The production factors which may be derived from determination of the concentrations of solubilized gases are gas partial pressure, percent saturation of adsorbed gas in a gas under-saturated shale, adsorbed gas content, bookable adsorbed reserves, critical desorption pressure, dewatering time, solution gas, stage of production, water salinity, identification of contributing seams and intervals, fluid density, dewatering area and volume, degassing area and volume, gas concentration, reservoir pressure, gas recovery factor, gas-in-place, optimum well spacing, optimum completion designs, including choice of which shale reservoirs or sections within a single shale reservoir to be produced in multi-zone wells and which wells in a pod should be produced first, second, etc., optimum production procedures including choice of which shale intervals and wells to produce first, second, etc., which to abandon or sell, effectiveness of prior completion and production activities, indication of regions and seams of favorable production potential, and other production factors which will be apparent to those skilled in the art.

Another aspect of the invention is an apparatus and/or system which measures the partial pressure of a hydrocarbon or another substance indicative of the hydrocarbon or measures a precursor variable such as the concentration of the hydrocarbon to allow or produce a determination of the hydrocarbon estimated ultimate recovery of the reservoir. The system may include a pressure transducer. The pressure transducer can measure the total pressure of the fluid at the measurement point. The transducer can also measure a gas pressure down a wellbore when the methane is evolved from the water.

Preferably, identification of hydrocarbon species and their concentration or partial pressure is measured by Raman spectroscopy. This may be accomplished by lowering a probe or housing within the well which contains the spectrometer or parts thereof or by guiding a radiation from a radiation source into the well and onto the fluid at or near the shale reservoir from the spectrometer located outside of the well. Characteristic radiation may also be guided from the fluid to the spectrometer located outside the well. Most preferably, the measurement is conducted on the fluid without first sampling the fluid. During sampling, the fluid is necessarily transported and disturbed. By measuring the fluid outside of an instrument package and in-situ the resultant concentration or partial pressure is more accurate.

This invention also describes a method of combining physical isolation of subsurface geological formations with spectroscopic analysis of fluids in order to quickly and accurately measure key properties of multiple intervals in a single wellbore. The method enables, in one embodiment, rapid assessment of each formation as a possible natural gas production target.

Alone, zonal isolation is well known and widely practiced, but is of use only in limited circumstances, such as when measuring fluid movement rates in order to evaluate permeability and skin damage. Alone, in situ downhole and surface spectroscopic fluid analysis has been perfected and commercially deployed, but it is challenged in some cases by the movement of fluid downhole between intervals in the wellbore, complicating analysis and interpretation of results when more than one interval is open to a wellbore.

By combining zonal isolation and downhole and surface spectroscopic fluid analysis in a specific manner, this invention provides the unexpected benefit of enabling in-situ measurement of fluid properties for multiple zones in a single wellbore without requiring an intervening cemented casing, allowing fast, accurate evaluation of multiple possible production intervals in a single well. The method further allows differentiation of fluids from each of these intervals, and thereby differentiation of the properties of various shale intervals penetrated by the well.

A further unexpected benefit involves the resulting ability to move fluids into and out of each interval independently, thereby providing the ability to obtain far acting reservoir fluids for analysis even in cases where fluid invasion into the interval has occurred.

A further unexpected benefit involves the resulting ability to combine a variety of complementary fluid physical and geochemical measurements, such as carbon isotope enrichment, fluid conductivity, fluid transmissivity, chemical composition and concentration measurements of solubilized gases, natural gas liquids and oils in a single operational test. The method is also suitable for use in a production test mode whereby the fluids are isolated downhole and then delivered to the surface for analysis.

Other objects, advantages and novel features of the present invention will become apparent from the following detailed description of the invention when considered in conjunction with the accompanying drawings.

SUMMARY

The present disclosure is comprised of:
a. an analytical method that establishes a thermodynamic equilibrium or known dynamic relationship between the concentrations of gases, natural gas liquids and oils or pressures of gasses in an isolated zone of a shale, or group of distinct shale gas intervals separated by non-shale formations, with the concentrations of fluids or pressures of gasses in a wellbore penetrating the shale interval or intervals;
b. an analytical method for identifying the chemical composition of gas, natural gas liquids and oils and determining their origin in an isolated zone of a shale, or group of distinct shale gas intervals separated by non-shale formations with the identification of chemical composition of gas, natural gas liquids and oils in a wellbore penetrating the shale interval or intervals;
c. a surface measurement apparatus capable of reliably performing the measurement ex-situ;
d. a downhole measurement apparatus capable of reliably performing the measurement in-situ;
e. a downhole straddle-packer assembly capable of isolating part of, or an entire shale;
f. various test modes to liberate fluids contained within shale reservoir matrix and fracture networks into the wellbore; and
g. analytical methods to equate these in-situ wellbore measurements with other various measurements or formation manipulations to a variety of formation production factors.

The methods are quantitative, accurate and reproducible. The methods includes strategies to remove interfering wellbore and reservoir properties, such as skin damage and low gas transport rates.

The disclosed methods includes the recognition that the partial pressure of methane and other hydrocarbons in a shale is equivalent to the partial pressure of methane and other hydrocarbons in a shale's pores. As a result, it is e.g., not necessary to directly measure the partial pressure of methane in a shale's pores; that value can be inferred by measurement of the partial pressure of methane in the fracture network.

Therefore, the disclosed measurement mode includes establishing a physical or chemical communication with one or more shale intervals and then analyzing fluid, gas or liquids from the matrix or fracture network of a shale, or group of shale intervals and performing trace analysis of solution gases and liquids within that fluid in order to establish the partial pressure of the gases and liquids.

When the partial pressure of methane and other gases in the interval is known, it can be used in a straightforward fashion to calculate the gas and liquids contents and thus gases-in-place of that interval. When sensing gasses in a wellbore penetrating multiple shale intervals that are not isolated from each other, the disclosed measurement mode will be able to identify the intervals with highest concentrations of particular gas species or liquids.

Because the disclosed method is designed to discriminate quickly, accurately, and inexpensively between intervals of varying gas-in-place, one apparatus available to use as part of this gas testing method has been adapted from zonal isolation straddle packer systems in some cases, or from simply collected open hole wireline logs over times shorter than crosstalk between intervals can occur.

BRIEF DESCRIPTION OF DRAWINGS

The accompanying drawings, which are incorporated in and constitute a part of the specification, illustrate preferred embodiments of the invention. These drawings, together with the general description of the invention given above and the detailed description of the preferred embodiments given below, serve to explain the principles of the invention.

DETAILED DESCRIPTION

The invention includes a method of reservoir evaluation and an apparatus to perform that method. An important aspect of the invention relates to correlation of the reservoir evaluation results with depth so that specific intervals can be targeted for drilling and completion.

In one embodiment, fluids, comprising gases or liquids, produced or withdrawn from a target formation can be measured by lowering a spectrometer on a wireline while recording signals that measure the concentrations of the fluids, gases or liquids versus depth. Logging speed can be adjusted to collect data faster or slower in order to capture data that describes the movement of those gases and liquids through the wellbore and thereby more accurately attribute those gases and liquids to the particular interval from which they originate. Wellbore treatments, such as adding acidified water, adding fresh water, adding hydrophilic solvents, or reducing or increasing wellbore pressure, may be undertaken, per normal industry practices. Additional data can be collected with other sensors, including but not limited to pressure, conductivity, temperature, video, spectral gamma, flowmeter and pH, concurrently or before or after the spectrometer data collection in order to enhance or enable subsequent data analyses. Any of these data collections can be repeated by multiple logs across the wellbore, or by collection of multiple data points at a stationary depth, in order to measure how the properties measured vary with time, or depth, with the well flowing or shut-in.

In another embodiment, fluids produced or withdrawn from a target formation can be measured by lifting, or allowing flow of, those fluids to the wellhead and into a sample cell in which pressure is controlled and to which a spectrometer is interfaced. The spectrometer and other sensors record that measure the concentrations of the fluids, gases or liquids and those concentrations are then correlated to the depth from which the fluids, gases, or liquids were produced. Wellbore treatments, such as adding acidified water, adding fresh water, adding hydrophilic solvents, or reducing or increasing wellbore pressure, may be undertaken per normal industry practices. Additional data can be collected with other sensors, including but not limited to pressure, conductivity, temperature, video, spectral gamma, flowmeter and pH, concurrently or before or after the spectrometer data collection in order to enhance or enable subsequent data analyses. Any of these data collections can be repeated by multiple data points over time, in order to measure how the properties measured vary with time.

Determination of Oil and Gas Shale Production Factors and a System to Determine Same The following is a description pertaining to examples relating to wells in gas under-saturated shale intervals, but it should not be seen as limiting the scope of the invention thereto.

Figure 1:
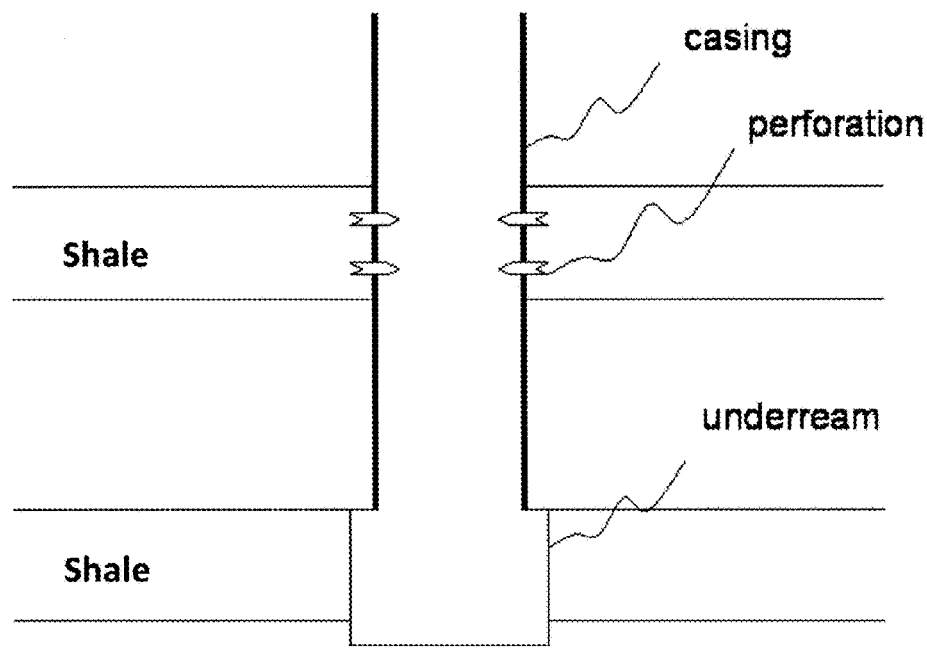
FIG. 1 shows a completed shale wellbore.

As seen in FIG. 1, a typical completed shale well includes a borehole which is drilled to at least a depth of a shale reservoir. During drilling and completion of the well an initial borehole is drilled to or through one or more shale intervals and a casing is set to at least the top of the lowest shale interval. Each shale interval of interest is then accessed from the wellbore either by perforating holes from the wellbore into the shale interval, or by open hole completion of the wellbore at the lowest shale interval. In many cases the wellbore contains water which originates from one or more layers of the geological strata, including some shale intervals, through which the borehole is drilled, or that may be residual from the drilling and completion process. In some instances water may be added to facilitate testing. In some instances the shale intervals of interest are partially or wholly saturated with water. In some cases the shale can be dry or partially dry which means that the shale has no or limited amounts of water. In some cases, shale intervals are stimulated or otherwise treated using techniques such as hydraulic fracturing, acid treatment, recirculation of water, and other known methods.

Typically, startup production from wells in gas under-saturated shale intervals will result in flowback of water from the shale. This water typically contains dissolved methane, termed "solution gas", or sometimes "solubilized gas". When the overall pressure in the gas shale interval is lowered to the critical desorption pressure of the methane contained within the shale matrix, further reductions in reservoir pressure lead to desorption of methane. Before this pressure is reached, in a shale gas interval that is under-saturated in gas, the primary fluid flow through the interval is water with solubilized gas. When pressure in the interval around the well falls below the critical desorption pressure, both gas and water flow through the interval towards the well. Gas flow is then due to expansion of the gas after it desorbs from the shale.

Depending upon the shale interval conditions and the shale type, depth and other geological characteristics, fluid from a well may need to be pumped for a very short time (e.g. not at all, if over pressurized with gas) or for a very long time (e.g. up to four years or longer for severely gas under-saturated shale intervals). The life of the well during which it produces economical amounts of methane, and the amount of gas that is produced during that time, also varies depending on the amount of methane entrained, contained, adsorbed or otherwise present in the shale reservoir.

Figure 2:
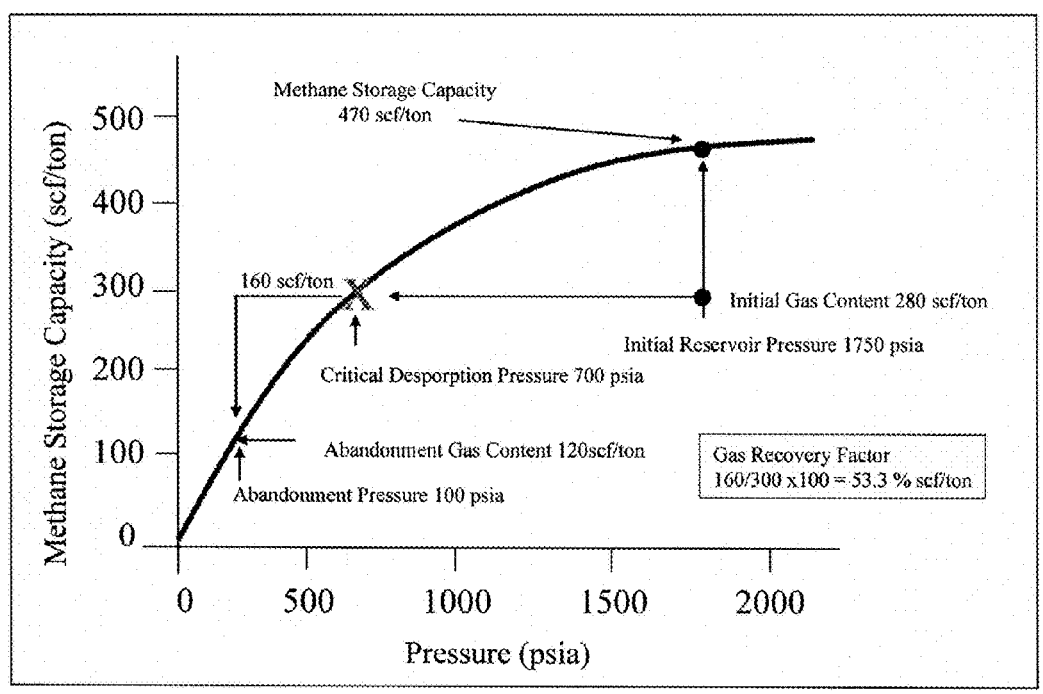
FIG. 2 shows a diagram of an isotherm calculation based on a gas content.

As seen in FIG. 2, a known method of determining the critical pressure which the well must reach in order to produce methane by desorption is by determining an isotherm of the shale or shale gas content curve which represents the amount of adsorbed methane the shale may contain depending upon the pressure. A sample of the shale from the interval itself is subjected to reduced pressure over time to measure the amount of methane which it contained. To this measurement is added a "lost gas" estimation to account for gas that issued from the shale sample during retrieval. The total amount of methane is then plotted on the isotherm chart and a correlation is made to the ideal curve. Where the saturation gas curve and measured gas content intersect is the critical pressure which must be reached in order for the reservoir to release the adsorbed methane. Other factors may be deduced from this plot or map.

Figure 3:
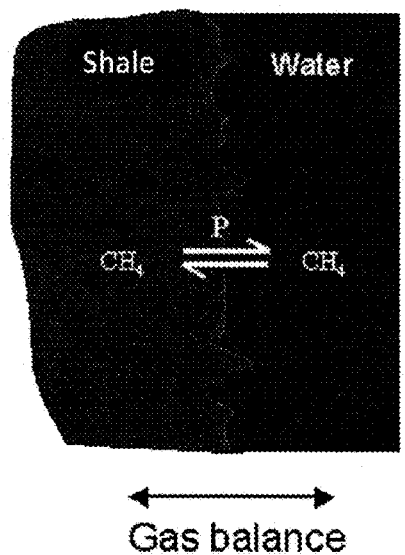
FIG. 3 shows a diagram of the shale interval fluid system in equilibrium.

As seen in FIG. 3 the methane present in the shale is interrelated to the methane of the reservoir fluid, which in turn is interrelated to the methane present in the well fluid. As the pressure is reduced on the well fluid, the pressure is in turn reduced on reservoir fluid and in turn reduced on the shale interval. Under some conditions, the shale interval, reservoir fluid and well fluid are initially at equilibrium. When one of these is changed the others are affected. The changes are not instantaneous. For example, a reduction of the pressure in the well fluid propagates from the well into the shale reservoir first affecting the pressure of the reservoir fluid and then the pressure of the shale reservoir. The propagation of the change, whether it is pressure, concentration of a substance or the like, may depend on many factors including the fluids, the shale intervals, permeability, porosity, density and fracturing of the shale. However, given time the change propagates as the system moves toward equilibrium by affecting the shale reservoir, reservoir fluid and well fluid properties.

When the methane present in the well fluid, reservoir fluid and shale interval are at equilibrium, these quantities are interrelated and a measurement of one can be correlated into a measurement of all of them. As the fluid pressure is decreased in the wellbore fluid, the fluid pressure of the reservoir fluid is reduced and the pressure of the shale reservoir is reduced. In response to this pressure reduction, in most instances, the reservoir fluid simply flows into the wellbore and becomes wellbore fluid as the two are hydrologically connected. As the surrounding fluid pressure of the shale interval is reduced the shale interval seeks the new equilibrium and intra shale fluid flow occurs. When the pressure of the gas under-saturated shale interval reaches the critical desorption pressure, methane gas begins to desorb and flow from the shale itself. This process is what occurs when the well is for example dewatered using a downhole pump. The water level or head is reduced so that the pressure is reduced and gas is produced.

During drilling the water or fluids are disturbed and mixed with other strata fluids. Given time the fluid or fluids come into equilibrium with each other and the reservoirs of the well.

The wellbore and reservoir fluids, as seen in FIG. 3, have an effect on each other as well as on the shale interval. A concentration of a substance in the fluid, a pressure or other variable can locally change for the well fluid. This in turn affects the reservoir fluid and the shale interval. The change propagates into the interval fluid and shale, and the system responds by seeking to reestablish equilibrium. When a continuous change is effected, such as when the well is continuously dewatered, a flux or gradient develops between the well fluid and the reservoir fluid and shale. If the variables of the change, such as permeability, rate of dewatering, rate of pressure change or other variables, are known then the concentration, pressure or the like may be calculated for a given point within the reservoir fluid or shale interval. This calculation may assist in determining the characteristics of the reservoir based upon a measurement of the well fluid when the well fluid is out of equilibrium with the reservoir. Thus, a measurement of the gas content or critical pressure of the methane for the shale interval may be calculated during dewatering, i.e. under non-equilibrium conditions. A computer model may be used to determine the flux or difference in concentration or pressure as well as measurements of other variables such as the porosity, flow characteristics or other flux variables present in the well and reservoir.

In the case of methane in shale reservoir fluids, the partial pressure of methane is directly affected by the amount of methane contained or present in the shale interval and by the ease with which that methane can adsorb, absorb or otherwise be contained within the shale. For a given shale interval, the more methane that is present in the shale interval, then the higher the partial pressure of methane in the fluids. Thus, the partial pressure of methane in the reservoir fluid is directly related to the amount of methane in the shale interval. For a gas under-saturated shale, as the fluid pressure is reduced, as with dewatering a well, reservoir fluid is transported from the shale interval to the wellbore. Once the partial pressure of methane at the depth of the shale interval equals the total fluid pressure, any further reduction in pressure causes the methane to transport off of or out of the shale interval as gas. An example of this is when dewatering causes the overall reservoir pressure to be lowered below the critical desorption pressure in a shale gas well and gas production to commence.

Therefore, by determining a partial pressure of methane in the reservoir fluid the methane critical desorption pressure in a gas under-saturated shale interval can be determined. As the partial pressure of methane is dependent on the amount of methane in the shale interval the partial pressure of methane does not significantly change for a system at equilibrium. The partial pressure of methane in the shale reservoir fluid remains constant as long as the fluid pressure is above the critical desorption pressure. This constancy of the methane partial pressure in the shale reservoir fluid can be observed, for example during a dewatering process when the hydrostatic pressure on the fluid is being continuously reduced. Thus, the partial pressure of methane of the reservoir fluid is the critical desorption pressure for the shale interval.

Figure 4:
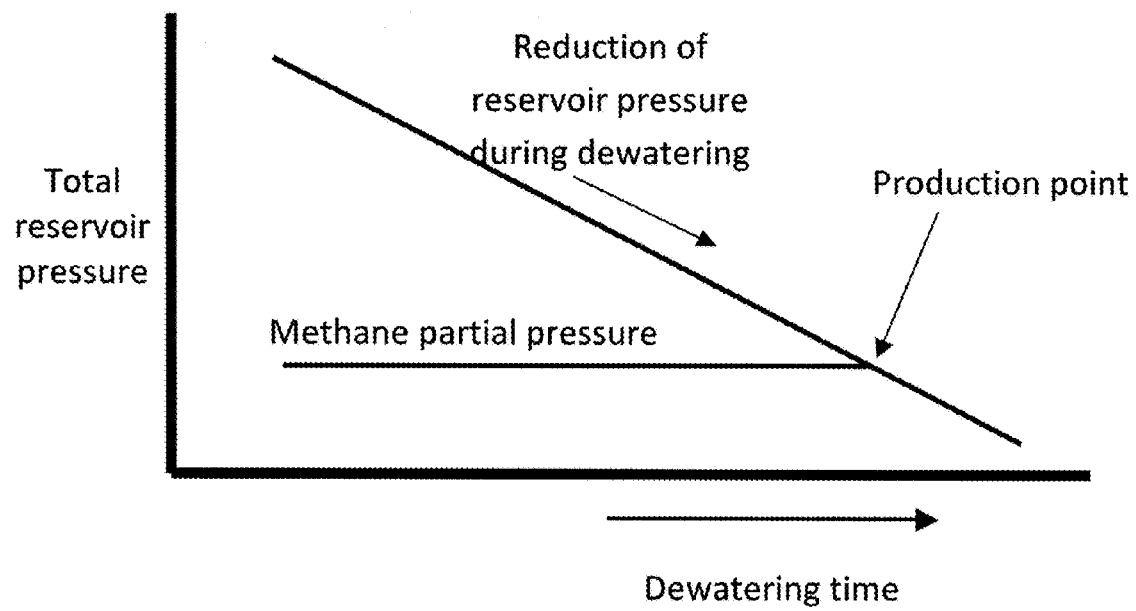
FIG. 4 shows a graph of a dewatering measurement.

As the partial pressure of methane of the reservoir fluid is interrelated to the partial pressure of methane of the well fluid, by measuring the partial pressure of methane of the well fluid the critical desorption pressure of a gas under-saturated shale can be determined. This, in turn, given an isotherm of the shale, can establish the adsorbed gas content of the shale interval, and can also aid estimation of the methane reserves within the shale reservoir. As shown in FIG. 4 the total reservoir pressure over time during dewatering of a gas under-saturated shale may be plotted based on a linear or fitted curve and compared against the methane partial pressure. The dewatering time may then be determined.

Direct measurement of the partial pressure of the methane in the fluid or fluids can be made by a METS sensor or a total gas pressure sensor with an appropriate filter. A measurement of a substance which is indicative of the methane partial pressure may also be used such as carbon dioxide or nitrogen or other substances which chemically or physically interact with the methane in the reservoir.

Another way of determining the partial pressure is by direct physical observation of the fluid in the well. In a wellbore, fluids near the bottom of the well can contain higher concentrations of methane and fluids near the top of the well can contain lower concentrations of methane. In other words, the saturation limit of methane in water increases with increasing pressure, which increases with increasing water head or depth.

For a wellbore fluid that contains dissolved methane, that methane will remain dissolved at depths where its concentration is lower than the saturation concentration and will cavitate as gas bubbles, to some extent, at depths where its concentration is higher than the saturation concentration. The depth at which cavitation commences is that depth at which the water head pressure is equal to the methane partial pressure. At depths above this point, the methane partial pressure exceeds the water head pressure and cavitation occurs. At depths below this point, the methane partial pressure is less than the water head pressure and cavitation does not occur. By observing the depth at which cavitation occurs, it is possible to calculate the partial pressure of methane in the wellbore fluid. Due to the well water being saturated with methane at every depth above that point, the well water will cavitate or form bubbles of methane at those depths. A video camera, acoustic device, bubble counter, thermocouple or other transducer of the like which is sensitive to the presence or evolution of bubbles in a fluid may be used to observe the depth at which the water head pressure is equal to the methane partial pressure. The pressure at this depth is then equal to the partial pressure of methane within the system or well fluid at the shale interval. This method of determining the partial pressure has several drawbacks in that other gases could be cavitating which would affect the observation and other dynamics of the well could offset the determination. In addition, supersaturation and nucleation effects in the fluid can introduce errors into the determination of the cavitation commencement depth. Another approach to determining cavitation is to use an optical spectrometer that can differentiate between the spectroscopic signature of methane dissolved in water and the gas phase methane in the bubbles. The difference in spectroscopic signature frequently manifests as a shift in the absorption peak or Raman scattering peak for methane or other gases indicative of methane, as well as changes in the width of such peaks. This method does not suffer from all of the drawbacks listed above, only the effects of supersaturation and nucleation, as well as dynamics of the well.

Another way of determining the partial pressure of methane within the system or well fluid is by capping the well and allowing the system to reach equilibrium. The capped well produces gaseous methane which fills the headspace of the well along with other gases. These other gases can be water vapor, carbon dioxide or other reservoir gases. By measuring the pressure of the head space the total pressure of the gases is obtained. Within this total pressure the partial pressure of the methane is included. If the other reservoir gases are subtracted out, by measurement or by assumption, or assumed to be near zero, then the resultant pressure is the partial pressure of the methane. As this partial pressure of methane would be the partial pressure of methane in the system the critical desorption pressure would be known. This method is similar to a sipper tube or canister which draws in well fluid or reservoir fluid and is taken out of the well for analysis of the partial pressure of the methane in a similar manner.

In such cases a sample of the reservoir fluid under reservoir pressure and temperature conditions in a sealed vessel or in a tube or other conveyance in which pressure is controlled—i.e. either maintained as constant or varied in a known and reproducible manner—is collected. The sample is allowed to come to equilibrium, or a relationship between the sample state and equilibrium is determined or estimated. The pressure of the vessel is measured, and the fraction of that pressure which is due to the gas or gases of interest is measured or assumed. From those quantities, the partial pressure of the gas or gases of interest is calculated Another example uses a sample collected and handled as above, in which localized, microscopic or macroscopic changes in vessel pressure are induced in order to induce gas evolution from the fluid. The system is allowed to come to equilibrium, or a relationship between the system state and equilibrium is determined. The pressure of the vessel is measured, and the fraction of that pressure which is due to the gas or gases of interest is measured or assumed. From those quantities, the partial pressure of the gas or gases of interest is calculated. This method has several drawbacks in that other gases including water vapor interfere with the measurement and creates uncertainty. The assumptions associated herewith as well as the necessity of having equilibrium in the well and fluid collection make this method undesirable.

Another example of determining the partial pressure directly is to submerge a vessel with a known volume, containing known or assumed fluids or gases and equipped with a gas-permeable membrane, into reservoir fluid or a wellbore, and the dissolved gases in the water are allowed to equilibrate with fluid(s) and/or gas(es) in the headspace, then the gas partial pressure in the headspace is measured with a pressure transducer or other transducer sensitive to the pressure, activity, fugacity or concentration of the gas or gases of interest. This can be combined with a sensor that identifies the fraction of the headspace volume (and thus partial pressure) that is due to the gas or gases of interest.

The fluid within the well may also be physically altered. In one example of this method to determine the partial pressure one may stimulate cavitation in a reservoir fluid using a source of energy such as a sonic gun or the like and correlate the extent of cavitation as a function of energy to the partial pressure of the gas or gases of interest. In another example of this method, the reservoir fluid may be heated using a variety of heating devices, including immersion heaters, microwave generators, or injection of steam of other hot fluids into a device, pipe or other container in contact with the fluid. The resulting increase in temperature will reduce the solubility of the methane in the fluid. The correlation of cavitation to heat input and/or temperature rise can be correlated to the partial pressure.

Of course another substance's concentration besides methane can also be measured to determine its partial pressure within the system. With this method the system should be at or near physical and chemical equilibrium in order to determine the partial pressure as it is at or in the shale interval.

Another example of a method of directly determining the partial pressure is to retrieve a volume of shale from the shale interval and seal the sample in a container at the reservoir conditions. This sample can then be allowed to off-gas methane in a sealed volume. When the sample comes to equilibrium the pressure in the sealed volume is the partial pressure of methane in the shale interval. This method is problematic in that retrieval of a sample without affecting the methane partial pressure of that sample is difficult.

Another determination of the partial pressure of methane in the fluid or fluids may be made by measuring the concentration of methane or other substance indicative thereof.

Figure 5:
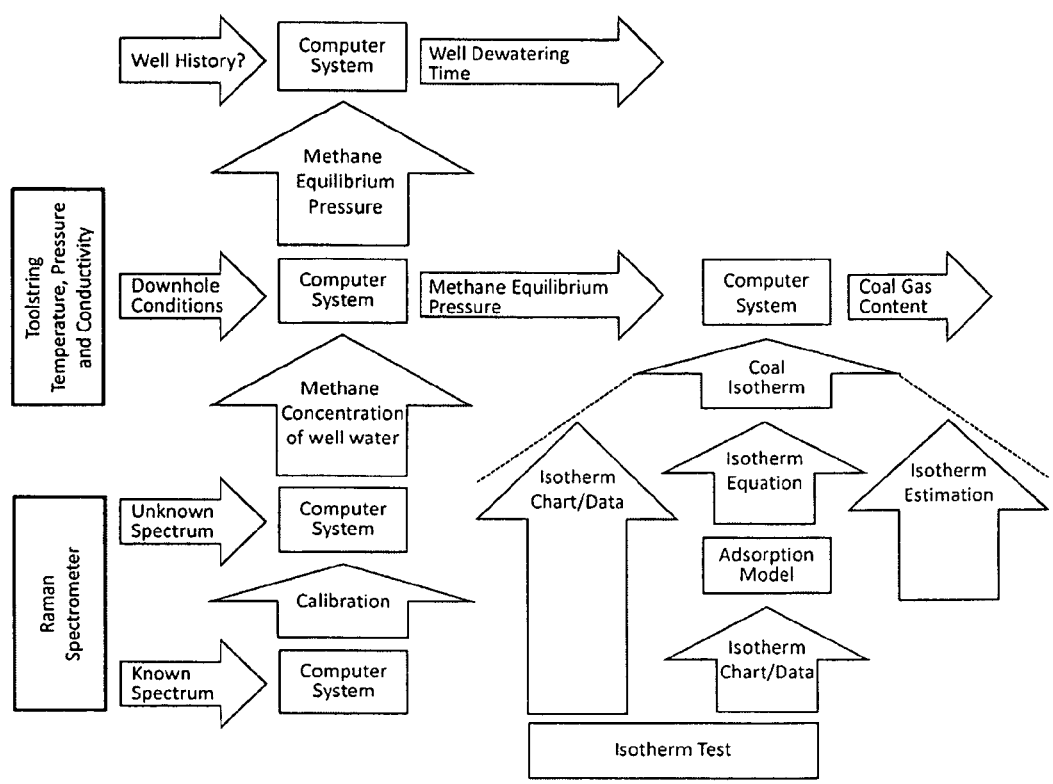
FIG. 5 shows a process diagram of the measurement system.

As seen in FIG. 5 the following example is directed toward a method involving measuring a concentration of the methane in order to determine the partial pressure of the reservoir fluid and in turn to determine production factors in a gas under-saturated shale, but should not be considered as limiting the method or apparatus.

A method of certain preferred embodiments of the invention involves measuring a concentration of methane dissolved in a shale reservoir fluid, correlating that concentration to a partial pressure of methane in the fluid, correlating that partial pressure to the partial pressure of methane in the reservoir, and correlating that partial pressure of methane in the reservoir to an adsorbed gas content in the shale as well as determining other production factors.

Figure 6:
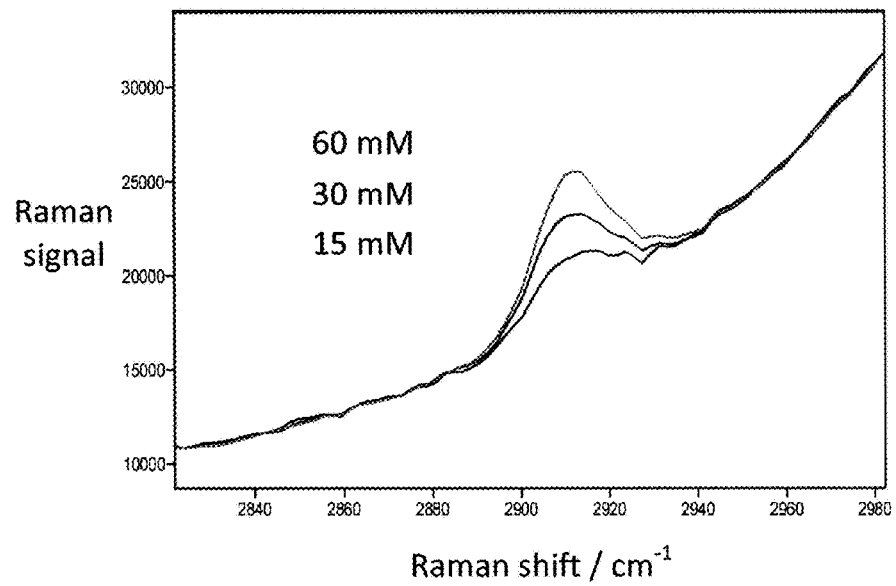
FIG. 6 shows a graph of a spectral signature for methane at three different concentrations.

For example, FIG. 6 shows the Raman spectral signature of methane dissolved in water for three different samples having different methane concentrations.

Figure 7:
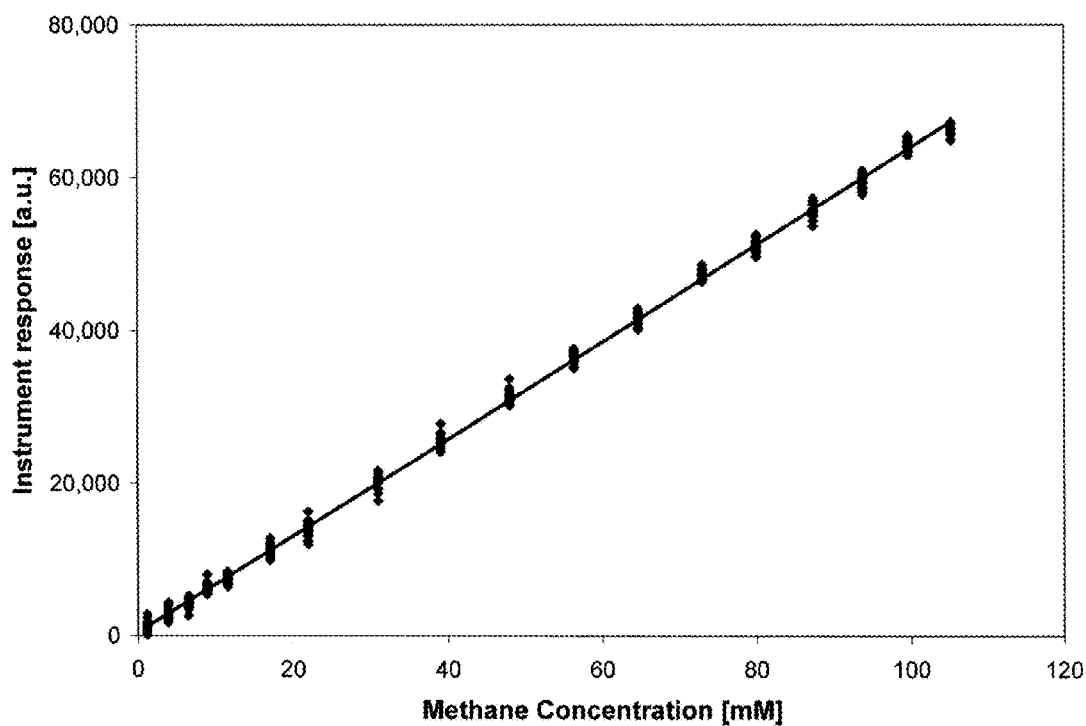
FIG. 7 shows a graph of a calibration between signal (i.e. instrument response) to methane concentration.

By correlating the signals measured for a series of samples with the concentrations of methane dissolved in the samples, it is possible to create a calibration between signal and concentration. FIG. 7 shows such a calibration for Raman signal responses to methane dissolved in water.

Dissolved methane concentration can then be calibrated to partial pressure of the methane in the reservoir fluid. For ideal fluids and conditions, this relationship is typically a simple linear relationship. For less than ideal fluids, or less than ideal conditions, this relationship may be complex. This relationship can be established for any fluid or condition by preparing samples of reservoir fluids under reservoir conditions, by impinging a partial pressure of methane onto the sample until the system is at equilibrium and by then measuring the concentration of methane. This process can be repeated for more than one partial pressure of methane until a relationship between dissolved methane concentration and partial pressure is established. Typically, the partial pressures impinged would be of magnitudes that include the partial pressure magnitude expected in the reservoir.

Figure 8:
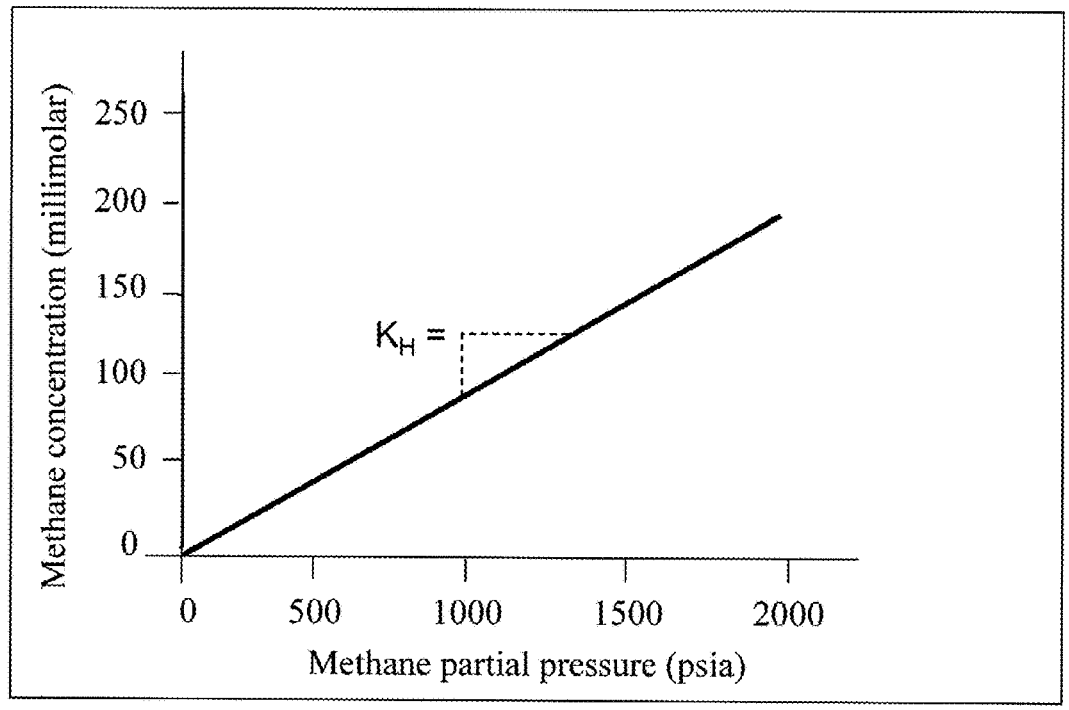
FIG. 8 shows a graph of a relationship between dissolved methane concentration and partial pressure of methane in a reservoir fluid.

For example, a relationship between dissolved methane concentration and partial pressure of methane typical of some shale reservoir fluids is shown in FIG. 8.

The methane partial pressure in a reservoir fluid can thus be determined by measurement of the dissolved methane concentration in that fluid.

The methane partial pressure in a reservoir fluid can then be used to determine the methane partial pressure in an overall shale interval. Under typical reservoir conditions, for fluids that are in physicochemical equilibrium with the reservoir, the methane partial pressure in a reservoir fluid or well fluid is equal to the methane partial pressure in the overall reservoir. For fluids that are not in physicochemical equilibrium with the overall reservoir, one may correct the partial pressure to reflect that state.

Figure 9:
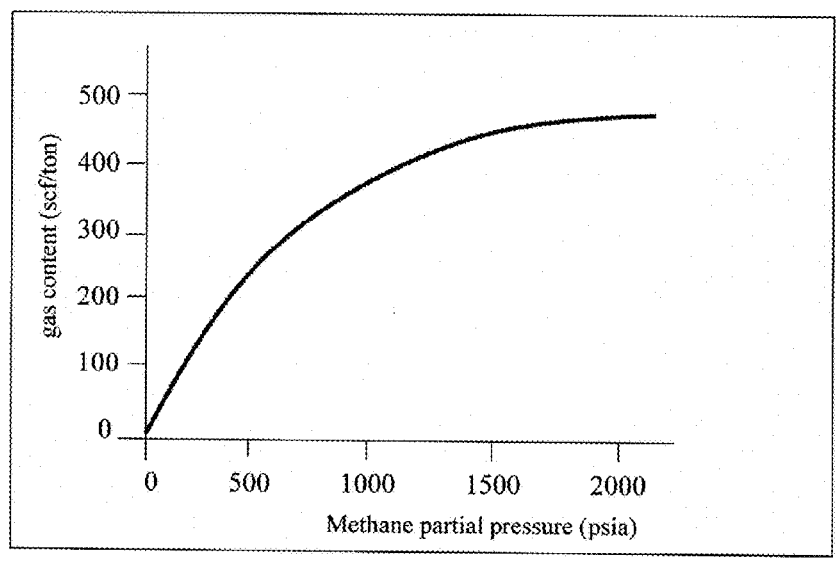
FIG. 9 shows a graphical representation of the relationship between methane partial pressure and shale adsorbed gas content.

The methane partial pressure in a reservoir can then be used to determine the adsorbed gas content of a gas undersaturated shale reservoir. FIG. 9 shows such a relationship typical of shale.

Thus, measurement of the concentration of methane dissolved in a shale reservoir fluid can be used to analyze quantitatively the adsorbed gas content of the shale interval.

Figure 10:
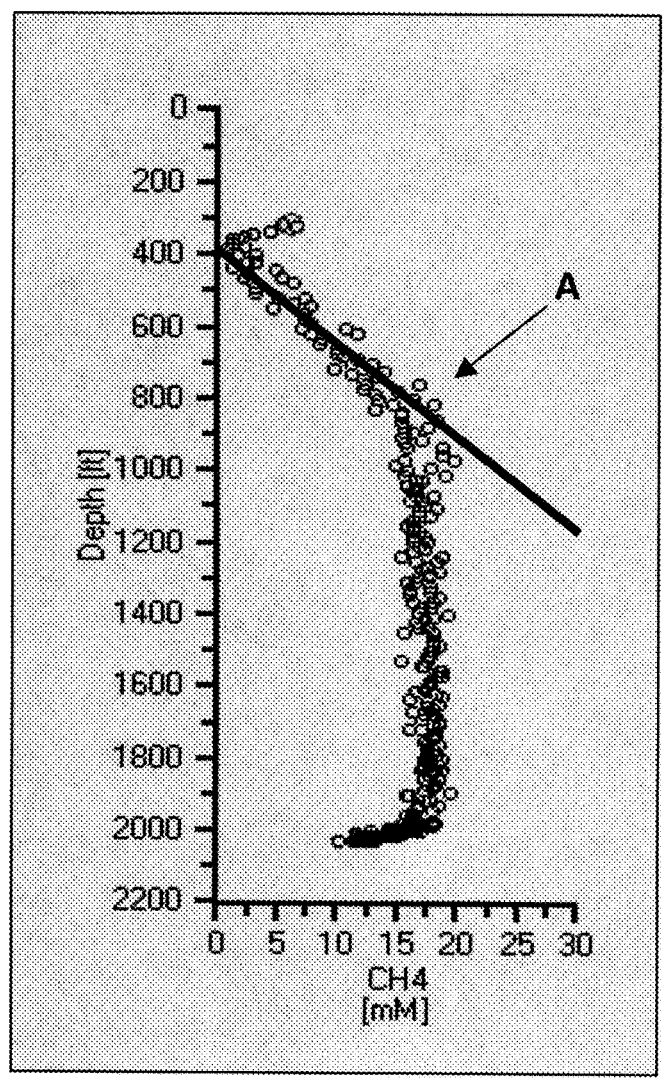
FIG. 10 shows a representation of a wellbore with concentrations plotted.

Another way of performing certain preferred embodiments of the invention are to measure the concentration of methane in the well at varying depths. This results in a plot of the concentration of methane versus the depth as shown in FIG. 10. The concentration of methane is shown plotted with Henry's law (solid line), or other models of the saturation limit of methane in water, against depth. As depth is increased, the measured concentration is saturated to a certain point A. At this point the concentration of methane in the water deviates from the saturation curve. This deviation point is indicative of the partial pressure of methane in the well fluid. The partial pressure of the methane in the well fluid is the head or pressure of the water at the deviation point. As the concentration of methane in a well does not change below the deviation point when the shale interval is not desorbing, even one methane concentration measurement below the deviation point can determine the partial pressure of methane by correlation to Henry's law or a saturation curve. With reference to the discussion above, cavitation would occur in such a well at any location in the well bore fluid above Point A.

Other measurements made in a wellbore or on wellbore fluids or gases can be combined with the methane concentration to provide a detailed understanding of the shale reservoir properties and stage of production. This process can include measurement and/or analysis of reservoir pressure, reservoir temperature, ionic strength of reservoir fluids, saturation limit of methane dissolved in water under reservoir conditions, depth and thickness of shale reservoirs, shale mineral content, shale masceral content, and other relevant variables.

Measurement of the dissolved methane concentration in a reservoir fluid can occur using a number of different methods and apparatus.

Measurements can be made downhole in a well that is drilled into a shale interval, and manipulated to contain the reservoir fluid. Such measurements can be made using an optical spectrometer, such as a Raman spectrometer. Such measurements can be made using a membrane-coated semiconductor sensor. Such measurements can be made using a mass spectrometer. Such measurements can be made using a sensor such as an optical spectrometer in tandem with a sample collector such as a formation tester or with a fluid control system such as a coiled tubing pump system. Such measurements can be made using a nuclear magnetic resonance spectrometer or a radio frequency, acoustic frequency, or microwave frequency spectrometer. Such measurements can be made using any transducer or sensor that provides a signal in response to methane concentration, including those transducers and sensors that may be less than quantitative in signal response.

Measurements can be made at the wellhead in a well that is drilled into a shale interval, and manipulated to contain the reservoir fluid. Such measurements can be made using standard laboratory analysis, e.g. via gas chromatography, on samples collected with various sampling apparatuses, including vessels that allow fluids of interest to flow into them and then seal, on samples that are collected at the wellhead using a pressure-regulated pumping system, and on other samples collected using methods obvious to those skilled in the art.

In some cases, fluids in a wellbore are not representative of a reservoir. For example, a wellbore drilled into more than one shale interval may contain commingled fluids that are representative of those intervals, in some ratio. In these cases, concentration measurements can likewise reflect the properties of those intervals, in some ratio.

Wellbores and wellbore fluids can be manipulated in order to ensure that the wellbore fluid properties, most specifically the methane concentration but also the temperature, pressure, ionic strength, and/or other physicochemical properties, reflect the reservoir properties of interest. For example, wells can be completed in only one shale interval so that other shale intervals or geologic intervals cannot contribute fluids to the wellbore. In another example, the wellbore fluids in a well drilled into a shale interval can be allowed to equilibrate with the shale interval until the wellbore fluids reflect the properties of the shale interval. In another example, the wellbore fluids can be extracted from the wellbore in order to induce fluid flow from the interval into the wellbore until the wellbore fluids reflect the properties of the interval of interest. In another example, multiple shale intervals in a well can be isolated using bridge plugs, packers, or other such apparatuses. The wellbore fluids in the isolated regions can then be allowed to equilibrate with the associated shale intervals, or one or more isolated regions can be evacuated with pumps or other mechanisms in order to induce fluid flow from the shale interval into the isolated regions until the fluids in the isolated regions reflect the shale interval properties of interest.

To manipulate wellbore fluids, the aforementioned formation tester, or other straddle packer assembly with a tester valve, can be used to extract fluid from the sidewall of a well until the fluid extracted represents the desired reservoir property. In one case, this could involve using the straddle packer assembly to extract fluid from one shale interval, in a wellbore that contains fluids commingled from more than one shale interval, until the fluid contained in the pipe above the straddle packer assembly reflects only the properties of that one shale interval. Then, the concentration measurement could be performed on that sample either at the surface or in the well.

Fluid manipulations can be used to draw fluids from various places in a reservoir, and thus provide the opportunity to analyze the properties of those places without drilling a well to them. For example, key reservoir variables of a shale interval near a wellbore can be analyzed by measuring the methane concentration and other properties of a wellbore fluid. The wellbore fluid can then be removed from the wellbore so that additional fluids flow from the shale interval into the wellbore. At some established time, the wellbore fluids can again be analyzed with the expectation that the fluids reflect the properties of the interval farther from the wellbore. In another example, a portion of the sidewall can be covered so that fluid is removed from the surrounding shale interval in only one cardinal direction. Thus, the rate of fluid removal, and the properties of the fluid and substances that it contains, can indicate reservoir properties of interest such as fracturing orientation, and dewatering and production volume aspect ratio.

Figure 11:
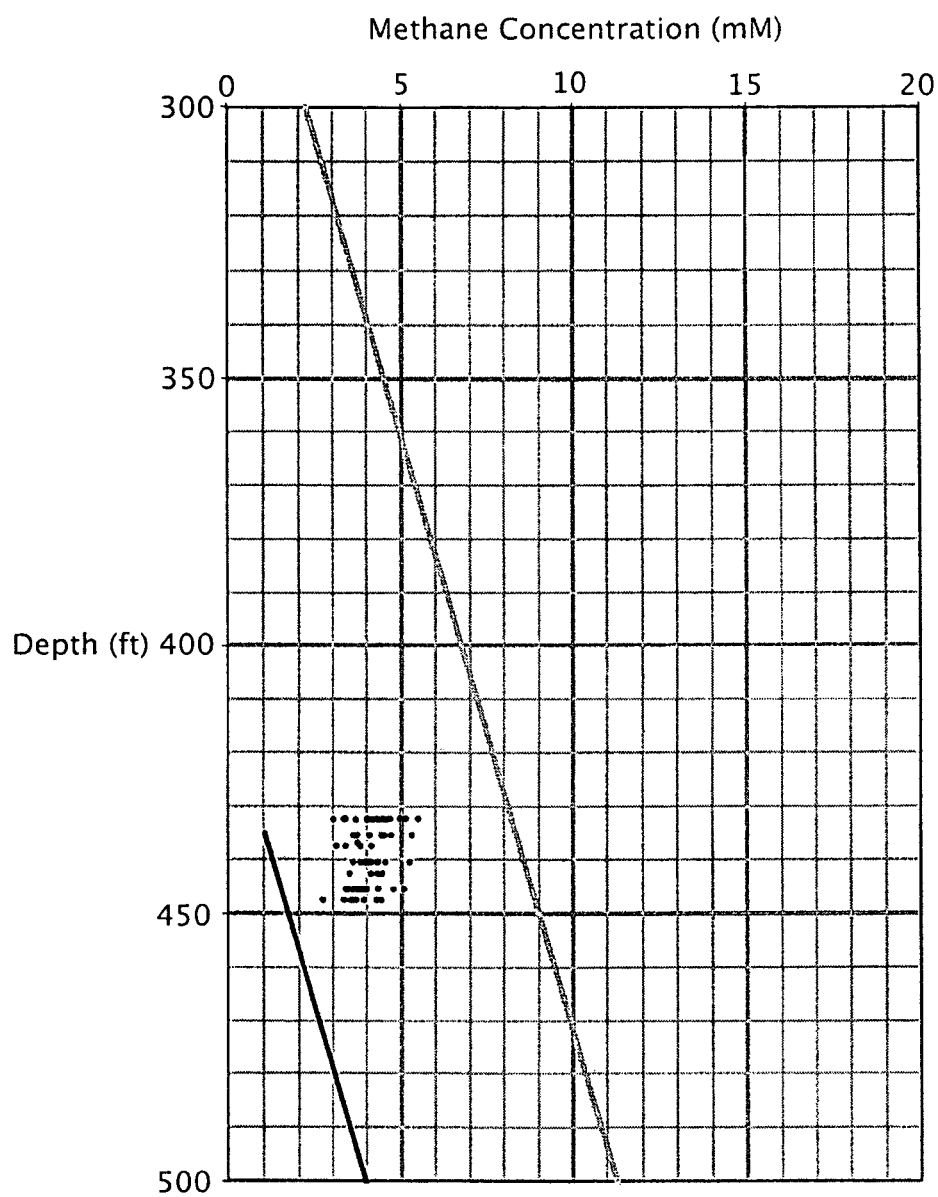
FIG. 11 shows a graph of a measurement when pumping is changed.

In one example of this technique, for a producing well that establishes a cone of depression near a wellbore, when the pump in that well is turned off the fluids from the surrounding shale reservoir flow into the wellbore. Near the wellbore, those fluids may be saturated in methane due to depressurization of the wellbore. Farther from the wellbore, those fluids may not be saturated because the cone of depression does not reach their region. By analyzing the methane concentration as a function of flow time, the cone of depression extent can be ascertained. This extent can be used to draw conclusions regarding whether the shale is being effectively depressurized and for how long the shale interval will produce gas at that pressure. As shown in FIG. 11 the Henry's law saturation curve during pumping is represented (solid line) as well as the saturation curve for when the pump is turned off (gray line). By measuring concentrations of methane (solid circles) after the pump is turned off and plotting against the saturation curves, the relation between the curves and the concentrations show how effective the well is being produced as well as indicating the slope of the cone of depression, and thus dewatering time and permeability. Concentrations of methane near the pump off curve indicate that the well is being produced effectively and that dewatering time has been long and/or permeability is high as well as a very small cone of depression. Concentrations close to the saturation curve for when the pump is on indicate that the cone of depression may be large and dewatering time has been short and/or permeability is low.

In some instances one shale interval can be extremely large. Some shale intervals may be 100 feet or larger in thickness. By measuring concentrations and chemical composition at different places along the shale the resultant partial pressures may be used to identify and determine production factors that may not be representative of one measurement. A cone of depression may actually be able to be identified if the cone of depression has vertical stratification along the shale. Other variables for the seam may also be determined via measuring along the entire width, such as locations of natural gas liquids production.

Measuring the concentration of methane and other higher hydrocarbons in a reservoir fluid, and analysis of other reservoir properties, thus allows analysis of critical desorption pressure for each gas species present, dewatering time and volumes, and other key reservoir and operating variables, such as locations of high natural gas liquids production.

Figure 12:
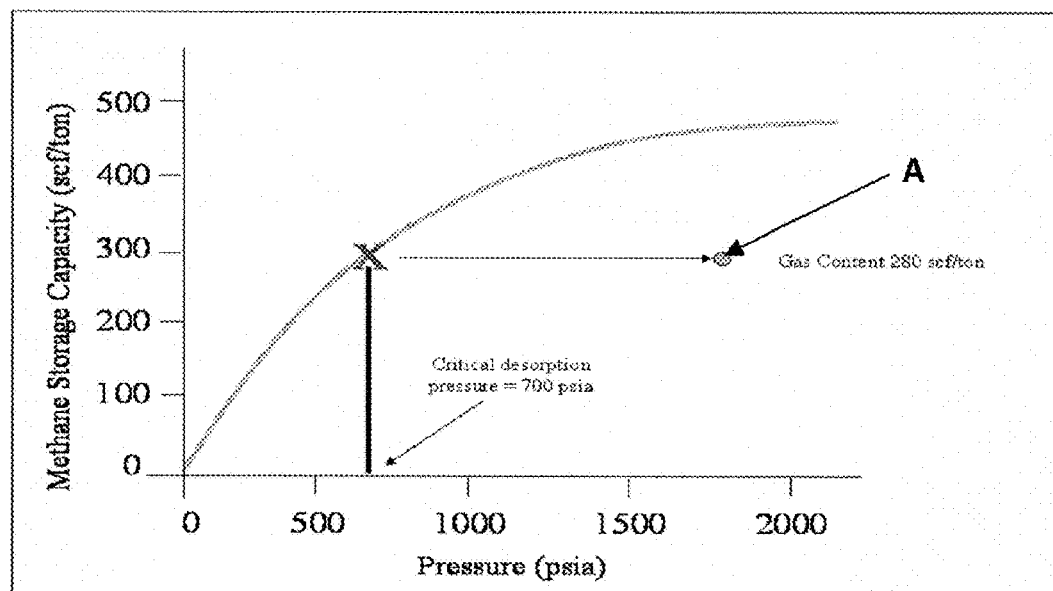
FIG. 12 shows a diagram of an isotherm calculation based on a critical pressure.

For example, FIG. 12 represents a plot of gas content and total reservoir pressure. The line indicates where in that space the shale adsorbed gas content is saturated. Measurement of methane concentration, and thus adsorbed gas content, for a shale interval at a certain reservoir pressure allows mapping of that particular reservoir onto this space. Intervals that adhere to the saturation line are saturated with gas. Intervals that do not adhere to the saturation line contain are under saturated with gas.

Point A indicates an example interval that is under saturated with gas. In order for gas to be produced from that shale interval, the overall pressure must be reduced until equal to the methane partial pressure, termed the critical desorption pressure. Thus, measurement of dissolved methane concentration allows direct quantitative analysis of critical desorption pressure.

In some cases, the saturation line is the same or nearly the same for more than one area of shale or more than one shale interval, allowing direct comparisons to be made. In other cases, the saturation line must be measured, e.g. by adsorption isotherm analysis of cuttings, in order to allow comparison.

Figure 13:
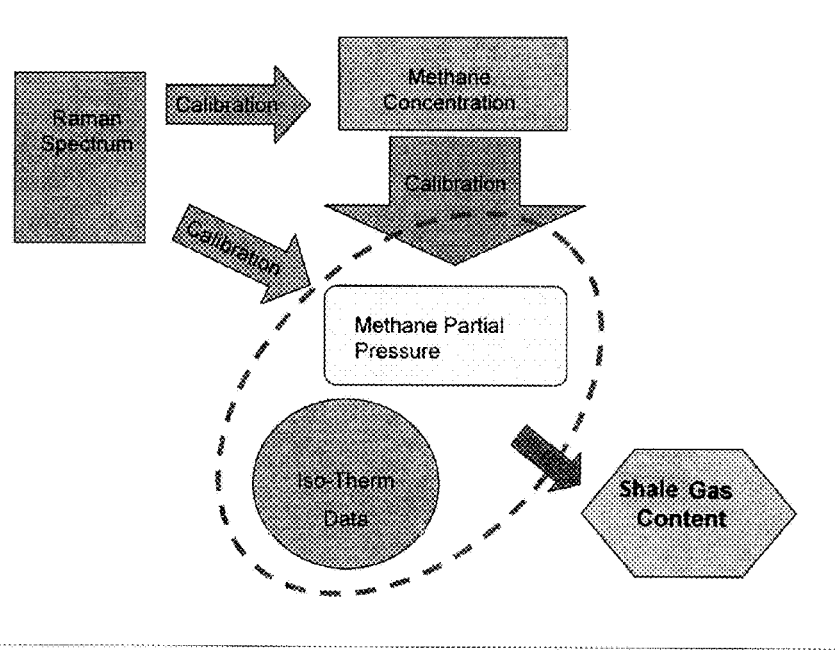
FIG. 13 shows a flow chart of measurements for a spectrometer.

Conversion of a Raman spectrum of shale reservoir fluid to an adsorbed gas content is based on scientific principles. An exemplary conversion process is summarized below and shown in FIG. 13:

1) Raman measurement.
   Raman, Temperature, Pressure, Conductivity.
2a) i) Conversion of Raman spectra to methane concentration.
   ii) Conversion of methane concentration to partial pressure.
2b) Conversion of Raman spectra directly to partial pressure of methane.
3) Convert methane partial pressure to adsorbed shale gas content.

Working in reverse order, to calculate the adsorbed gas content, the partial pressure of methane in the fluid surrounding the shale interval and the isotherm of the shale are provided. The isotherm is a correlation, at a given temperature, between the partial pressure of methane and the adsorbed storage capacity of the shale interval, i.e. saturated methane gas content. The isotherm should be known or estimated externally to the Raman measurement. Thus, the goal in making the Raman measurement is to determine the partial pressure of methane in the fluid surrounding the shale interval.

In order to make this conversion between a Raman spectrum and methane partial pressure, the instrument is calibrated. This is done by one of two methods. Both involve preparing samples of methane in equilibrium with water at various pressures. Raman spectra of the samples are taken. The pressures of the samples should correlate with the range of methane partial pressures expected in the unknown samples.

The concentration of methane in each sample's fluid can be calculated by Henry's law, using an appropriate Henry's law constant for the given conditions, i.e. temperature, salinity and methane partial pressure, or by some other method that indicates the solubility of methane in water. This methane in fluid concentration can then be correlated with the intensity of the methane peak in the Raman spectra of the sample. This method is robust and has several advantages.

Alternately, the partial pressure of methane can also be directly correlated with the intensity of the methane peak in the Raman spectra.

With the above correlations, either methane concentration or partial pressure can be calculated by measuring the Raman spectrum of an unknown sample. Correlating directly to partial pressure, while simpler, introduces a larger possibility for error, as the unknown fluid may not have the same relationship between dissolved methane and partial pressure, i.e. Henry's law constant (or other solubility relationship). Conversely, correlating to concentration and then to partial pressure provides the advantage that the relationship between concentration and Raman signal will not be affected by differences in the fluid quality, without it being obvious in the Raman spectra, example: an unknown peak in the same spectral range as the methane. Subsequent conversion of methane concentration to partial pressure uses Henry's law and a Henry's law constant that is corrected for the unknown sample's temperature and salinity, which can be measured in a wellbore, for example. In both of these methods the partial pressure of methane is calculated. This then allows a direct reading from the isotherm to determine the gas content.

Many factors such as localized depressurization may be taken into account when determining the partial pressure.

Another example of the steps to determine the partial pressure based upon an optical measurement of the methane concentration to reach partial pressure is as follows. First, construct a calibration of Raman or other spectrometer counts that relates those counts to methane concentration dissolved in water (preferably, an ideal water such as deionized water). This requires that one first apply a methane partial pressure at a room temperature and allow the system to come to equilibrium; preferably this is done for a pressure range that exceeds the range of interest in the well. Then, one measures the Raman signal from the methane in the ideal water sample and calculates the methane concentration dissolved in that sample. Then, one can correlate this concentration with the methane partial pressure that was applied, using a Henry's law constant for water at room temperature. This gives a calibration between Raman signal, concentration in the water and partial pressure of methane above the water at room temperature.

Function is:

moles of $CH_4$/moles of water=Pressure[atm]*Henry's constant

[mM]$CH_4$=Pressure[atm]*Henry's constant*55 moles of water/liter of water*1000

Second, record the Raman spectra of the unknown well sample, and its temperature and salinity.

Third, from the Raman measurement and the calibration, a concentration of the methane in the well water is calculated, via computer or model.

Fourth, with the methane concentration and a value of the Henry's law constant for the particular well temperature and salinity, calculate a methane equilibrium partial pressure. Values of Henry's law constant for temperatures and salinities of interest are available in published literature, or can be measured in the laboratory.

Fifth, obtain or generate a relationship between saturated shale gas content at the reservoir temperature versus methane partial pressure, where the shale is in a saturated moisture state, i.e., at its equilibrium moisture content. This can be a general isotherm for the type of shale or, for more accuracy, the exact shale from the well.

Sixth, using the equilibrium methane partial pressure for the well conditions (methane content, temperature and salinity), calculate a gas content for the shale interval from the isotherm. With a valid isotherm for the shale interval, the absorbed methane content of the shale can be read off the isotherm with the partial pressure of methane. Another option is to use a Langmuir or other type of isotherm model equation to represent the true isotherm. The Langmuir and other model equations are equation versions of the isotherm. Using these one can calculate the gas content with the equation. Lastly, the accuracy of the values used for the Henry's law constant and the shale isotherm will have an effect on the accuracy of the calculations.

As described above, by measuring the partial pressure of methane or another indicative substance or by correlating the concentration of methane to partial pressure a production value can be obtained. The use of an ideal gas content curve or shale isotherm is needed in order to determine the shale adsorbed gas content. As mentioned earlier a cutting or core sample of the shale may be used to determine the actual shale isotherm. However, an isotherm from a similar shale may be used as well as an isotherm which is representative of a shale, shale type, shale formation or shale basin/region. In such an instance a library of shales may be compiled in order to allow automated determinations based on the shale. This may result in a range of values dependent on the isotherms used. Another example of automating the determination of the shale gas content is by using a model based upon equations.

Below is a method of determining the adsorbed gas content from the partial pressure of methane via an isotherm model for a wide range of shales. In this model the actual shale isotherm for the shale being measured need not be measured. However, to achieve a more accurate adsorbed gas content an actual cutting or core and measurement of the shale can be done to determine the isotherm for the specific shale reservoir.

The correlation goes from $P_m$ (methane partial pressure, which is obtained from the methane concentration and the appropriate value of the Henry's law constant) to G (adsorbed shale gas content).

The Langmuir equation is:

$$\theta/(1-\theta)=Ka;$$

where $\theta$ is fractional gas coverage or gas content (i.e. $\theta=G/G_{sat}$ with $G_{sat}=G$ at saturation, in scf/ton), K is the binding constant for methane to the shale and a is thermodynamic activity, which is related to concentration and to "partial pressure of methane", $P_m$.

By analogy, a new Langmuir isotherm is defined:

$$G_{sat}\{\theta/1-\theta\}=K_bP_m$$

where, $K_b$ is the binding constant for methane to the shale in scf/ton psi. This formulation has G approaching $G_{sat}$ as $P_m$ goes to infinity. Now, using $q=G/G_{sat}$ $$G/\{1-(G/G_{sat})\}=K_bP_m;$$

$$G=K_bP_m-\{GK_bP_m/G_{sat}\};$$

$$G\{1+(K_bP_m/G_{sat})\}=K_bP_m$$

And finally, $$G=(K_bP_m)/\{1+(K_bP_m/G_{sat})\} \qquad \text{Equation 1}$$

With this comes G (shale adsorbed gas content) from $K_b$ and $P_m$. The linearized reciprocal equation is:

$$1/G=1/K_bP_m+1/G_{sat} \qquad \text{Equation 2}$$

Figure 14:
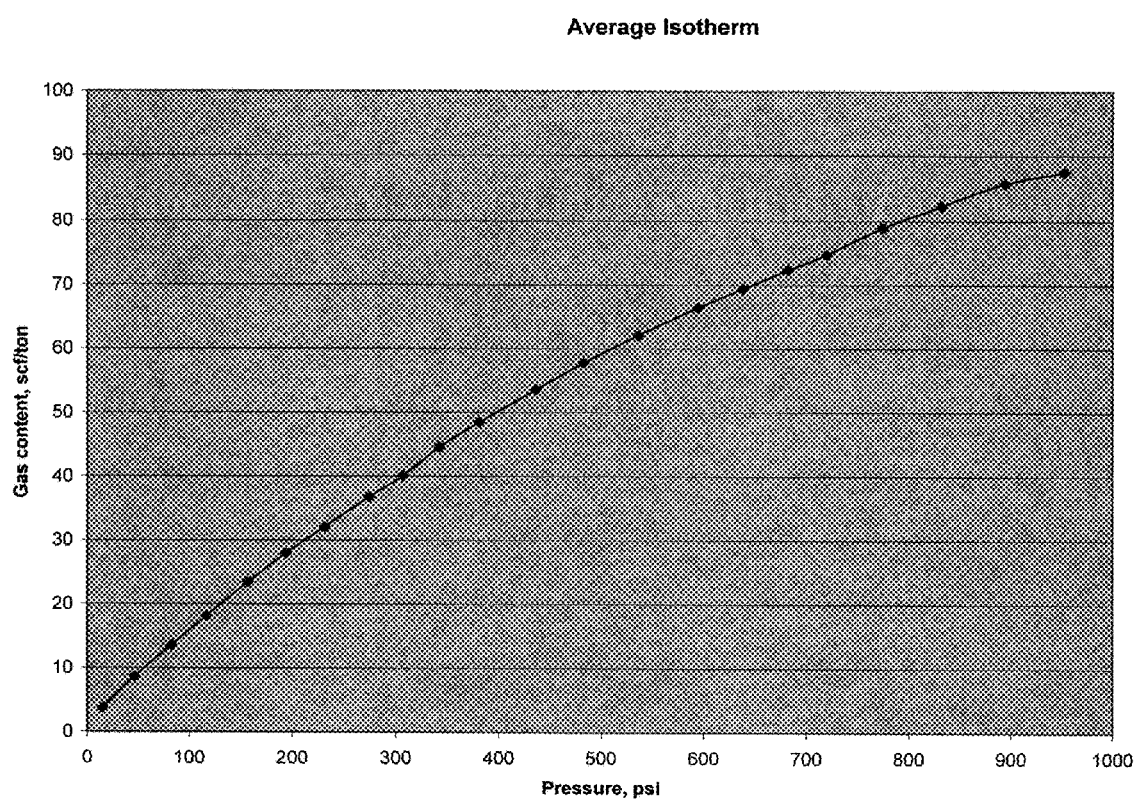
FIG. 14 shows an averaged shale isotherm.

This linearized reciprocal equation was used to analyze the isotherm shown in FIG. 14 below (i.e. plot 1/G versus 1/P, which gives $1/G_{sat}$ as the intercept and $1/K_b$ for the slope). This gives an R value of 0.99953. It gives $G_{sat}$=178 scf/ton and $K_b$=0.175 scf/ton psi.

Figure 15:
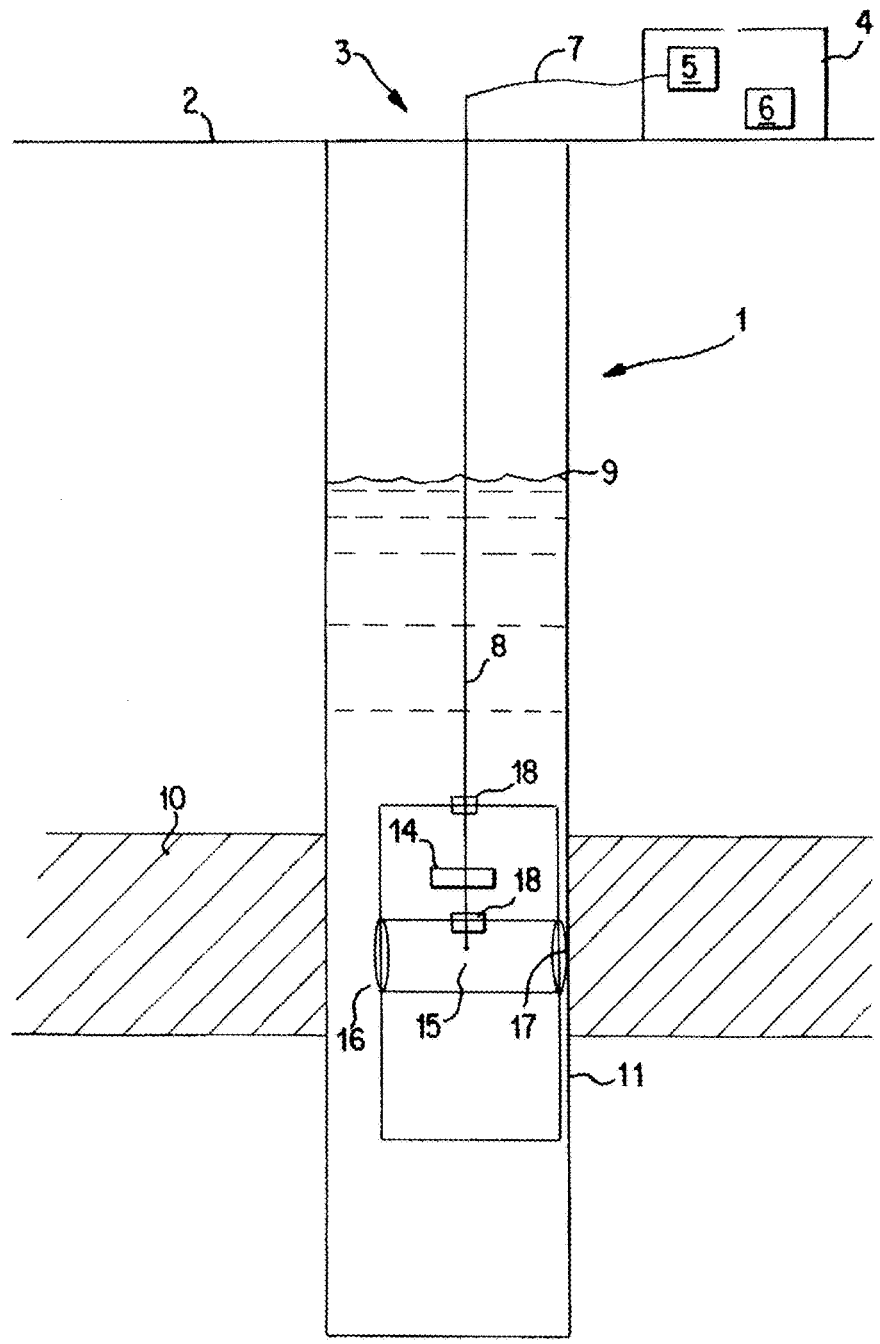
FIG. 15 shows a diagram of a measuring device.

Using Equation 1 above with these values, one can enter any value of $P_m$ and obtain the corresponding value of G for shales for which the typical isotherm in FIG. 15 is suitable. To predict the isotherm a bit more closely reiterations and other modifications can be done.

Methods of directly determining or measuring amount of gas in a shale interval or region of a shale interval can include, but are not limited to, spectroscopies in which energy travels into the shale interval and interacts with methane or substances indicative of the amount of methane. Examples include acoustic spectroscopy, microwave spectroscopy, ultrasonic spectroscopy, Raman spectroscopy, reflectometry, and the like. In an example case, microwave radiation of the appropriate wavelength is impinged on a shale interval, travels through the shale to an extent that allows sufficient interaction with methane, and a method of detection based on that interaction that provides the amount of methane entrained in the shale interval is used. That amount of methane is related to the adsorbed gas content of the shale.

The apparatus to carry out certain preferred embodiments of the invention includes as shown in FIG. 15 a partial pressure sensor or measuring device and a comparator for comparing the methane partial pressure to the isotherm. In one embodiment the partial pressure measuring device includes a concentration measuring device and a calibration system to calibrate the concentration of dissolved methane to the partial pressure. The apparatus may include other sensors such as a temperature sensor, salinity sensor and/or a pressure sensor. The measurements for each of these may be used by the calibration system in order to determine the methane partial pressure.

The system used to measure the concentration may also contain other measuring devices for salinity or electrical conductivity as well as temperature and pressure. Preferably, the system will measure the temperature and the electrical conductivity of the reservoir fluid with the concentration. This will allow a more accurate determination of the methane partial pressure in the reservoir fluid. Alternatively, salinity can be determined by analyzing the distortion seen in the water O—H stretch Raman peak present in the acquired spectra. The O—H Raman peak is a composite of both symmetric and asymmetric stretch modes. It is well known that the height ratio of the individual symmetric and asymmetric modes varies with increasing salinity.

A system which includes a concentration sensor for use downhole may be preferable due to its size and speed. An optical instrument for use down a well is comprised of a radiation source which is directed through a series of optical components to a sampling interface where the radiation interacts with a sample that is outside of the instrument and across this interface. The returning radiation is then directed through a series of optical components to a spectrometer. A controlling device inputs operating parameters for the spectrometer and packages spectral data for delivery to an uphole computer. The entire instrument is packaged in a steel housing, with additional sensors for pressure, temperature, and conductivity incorporated into the housing endcap. The instrument is attached to a cable head and lowered into a wellbore by a wireline winch. The uphole computer and software allows a user to set operating parameters for the instrument and graphically display data delivered from the controlling device.

A calibration file is created by correlating response and spectra of dissolved methane to known concentrations of dissolved methane. The calibration file is used to predict methane concentration from the spectra delivered uphole by the instrument. Several additional calibrations are created at various temperatures and salinities to develop a library of Henry's law constants to be used in order to calculate methane partial pressure. The values of temperature and conductivity measured downhole are used to choose an appropriate Henry's law constant from the library and calculate a methane equilibrium partial pressure for the interval from the concentration measured by the instrument. This methane equilibrium partial pressure is the critical desorption pressure. As the total pressure (hydrostatic pressure) falls below the critical desorption pressure, the well begins stable gas production.

Once critical desorption pressure is known for the interval, gas content is calculated using the value for critical desorption pressure in conjunction with an isotherm that is representative of the shale's ability to sorb methane. An isotherm is a plot of total methane pressure with respect to a shale interval's holding capacity for methane, in standard cubic feet of gas per ton of shale. A technique as described above may be used to determine an isotherm.

The rate at which the hydrostatic pressure head (water level) can be lowered depends on the discharge rate of the pump, the well completion method, relative permeability of the interval and interval recharge rate. By noting the static water level before water discharge begins, one can monitor the hydrostatic pressure drop with a pressure transducer attached just above the pump and determine the rate at which the hydrostatic pressure drops with respect to total water discharge. This rate can be used to predict the time need to reach the critical desorption pressure of the well or the dewatering time as described above.

The depletion area of water from the interval, or cone of depression, can be modeled using hydrological assumptions and water discharge rates to determine the lateral extent of interval at or below the critical desorption pressure and actively contributing to stable gas production.

As the exemplary descriptions have been used to explain the invention with regard to shale methane they should also be considered to include the determination with regard to other carbonaceous formations, and they should be considered to include the determination with regard to carbon dioxide, nitrogen, other hydrocarbons, and other gases, including natural gas liquids, in addition to the methane as mentioned. The exemplary descriptions with regard to measuring or determining concentration and the production factors should also be considered to include other precursor variables and is not meant to be limiting.

Apparatus and Method of Combining Zonal Isolation and In Situ Spectroscopic Analysis of Reservoir Fluids for Shale Reservoirs A number of methods familiar to those skilled in the art can be utilized in order to increase further the accurate correlation of the results with depth of interval by isolating a particular interval physically in order to enable interacting with a particular interval separately from others that may be intersected by the wellbore. Such interactions may include instigating changes in fluid flow, pressure, or other physical or chemical properties from the wellbore to the interval, or allowing or encouraging changes in similar properties from the interval to the wellbore. The results of those interactions can be that fluid samples or physical properties such as pressure transients that represent the reservoir properties of the interval can be collected or analyzed in situ in order to calculate those reservoir properties. The methods of isolation include but are not limited to: testing on penetration, before other potentially interfering intervals are intersected by the wellbore; setting retrievable or non-retrievable bridge plus, in order to isolate an interval targeted for testing from other intervals occurring at greater depths; using swellable packers either in a straddle mode or in a single packer mode to isolate the target interval from other intervals in the wellbore; and exploiting flow rates of fluids with or without active pumping in order to attribute the properties of flow streams analyzed at different times to intervals at different depths.

One apparatus allows ready attribution of fluid properties to the correct formation by actively isolating intervals in a wellbore, drawing out fluid from each formation, analyzing such sample, and thereby analyzing the production factors of interest in that formation.

This apparatus includes isolating the intervals by using pack-off technologies, and/or by using active pumping to favor production of fluids from a particular interval, in conjunction with or instead of wellbore treatments. Sealing mechanisms for isolating hydrocarbon bearing zones are readily available throughout the industry, commonly referred to as straddle packers, and the like. A variety of packer types are available which can be used to enable the current invention, including pressure set inflatable packers. These mechanisms are deployed with a variety of complementary tools such as valves, sensors, samplers, pumps, etc. The valves can be manipulated by using pressure applied down the inside or outside of the deployment work string, rotation of the work string, changes in compression applied to the work string, or vertical movement of the work string, with all types being compatible for use with the present invention.

Figure 16:
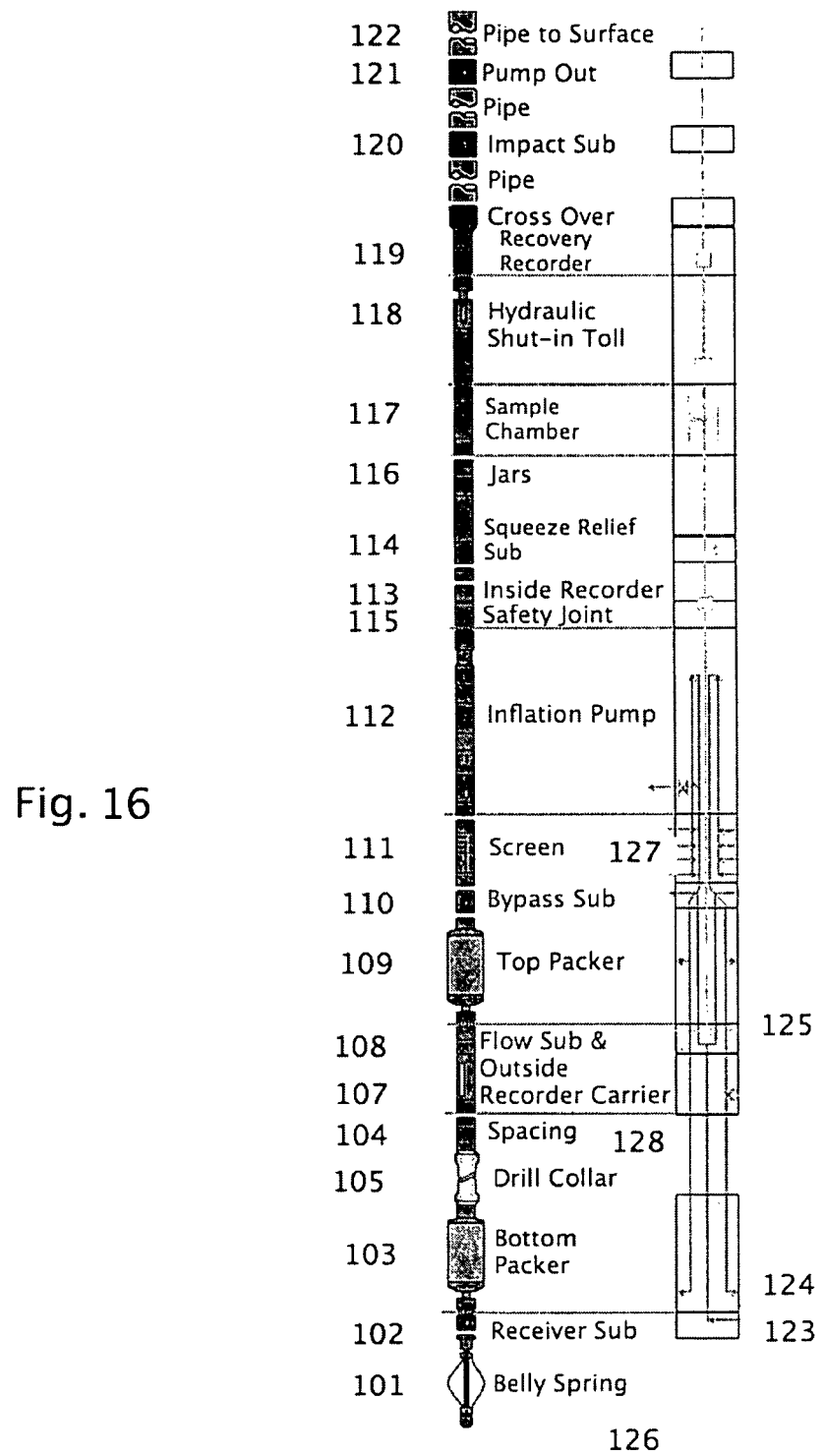
FIG. 16 shows a diagram of one example of a downhole apparatus with zonal isolation packers that can be used to perform the disclosed method.

FIG. 16 illustrates one embodiment to effect the disclosed invention based on use of an inflate-style test string with no external umbilicals or power cables, that is deployed on a tubing work string, and either a downhole spectroscopic analyzer, a surface spectroscopic analyzer or a surface spectroscopic analyzer that is coupled to a downhole sensor analysis chamber using optical fibers. In this case the test string is lowered into a well on a work string. It is positioned in front of a shale interval, and the packers are used to isolate that interval from the remainder of the wellbore, and especially from other intervals in the well. A valve situated at the bottom of the work string is then opened to allow pressure communication with the target interval. Then, a variety of methods, including but not limited to blow-downs, whereby the fluid level in the work string is evacuated up the well-tubing annulus by pressure acting on the surface of the fluid, swabbing, or by circulating fresh water, can be employed to induce flow of fluids from the shale interval into the work string. Properties of the produced fluid at the bottom of the work string as a function of depth and time can be determined using either a down hole spectroscopic analyzer deployed on a guide wire with electrical conductors, or a guide wire with a set of optical fibers connected to a spectroscopic analyzer situated at the surface, or by moving the produced fluid, gas and/or liquids to the surface for analysis with a spectrometer or other sensor system. The guide wire is then pulled out of the work string. Blow-down and/or pumping and subsequent spectroscopic analysis cycle can be repeated to validate results or until the fluid properties at the bottom of the work string reach a steady state or other condition, where this condition indicates that the fluid properties including composition, concentration and partial pressure can be related to the authentic reservoir in the interval.

Under such conditions measurement of the fluid properties allows determination of selected properties of the interval, such as its ethane content and the originating depths within the shale of ethane production, as described above. After the measurement, the packers may be released which allows the test string to be moved to a second interval in the wellbore. The measurement and analysis described above may be repeated, allowing the determination of the properties of the second interval. This process may be repeated until substantially all of the hydrocarbon-bearing intervals in a given well have been analyzed. This method allows the analysis of the gas and liquids content for each of the seams in a multi-seam well.

FIG. 16 further illustrates a belly spring 101 is run on the bottom of the tool string to provide drag and prevent rotation of the straddle packer assemblies 103, 109 during the inflation & setting process. A receiver sub 102 sits above the belly spring and below the bottom straddle packer 103. This sub allows pressure in the sump 126 to equalize with annulus pressure 127 above the top straddle packer 109 via an internal conduit 123 connected to bypass sub 110.

The Straddle Packer Assemblies 103 and 109 are comprised of a chassis and an interchangeable, inflatable, rubber element. These elements can vary in length. The Top Straddle Packer 103 contains an inner mandrel to accommodate internal conduit 123 and conduit 124 used to set and maintain pressure in the two Straddle Packers 103 & 109, while the other Straddle Packer 109 also accommodates conduit 125, which provides a path for fluids between the test interval 128 and work string 122. Spacing pipe 104 and/or drill collars 105 are used to span the height of test interval 128. Bypass pipe 106 is run inside the spacing pipe 104 & drill collars 105 to accommodate conduits 123 and 124. The outside recorder carrier 107 carries two electronic memory pressure gauges (EMPG or gauges) to record formation pressure and straddle packer inflation pressure. The flow sub 108 allows fluid exchange between the test interval 128 and conduit 125. It also accommodates the other two conduits.

Screen filter 111 filters out all coarse particles in the wellbore fluid drawn into the inflate pump 112. It consists of an outer perforated case, a fine inner screen and two inner mandrels to accommodate all three conduits 123-125. Both straddle packers are inflated by repeated clockwise rotation, and deflated by compression and discrete clockwise rotation, of the inflate pump 112, which incorporates an interchangeable pressure relief valve dictating the maximum straddle packer inflation pressure. The inside recorder carrier (IRC) 113 includes two gauges to record formation pressure. If pressure inside the conduit 125 increases above hydrostatic due to fluid squeeze generated during inflation of the packers it is released into the annulus 127 through the squeeze relief sub 114. If blow-down operations are used to withdraw fluid from the shale reservoir into the work string 122 the squeeze relief sub 14 is not used.

The safety joint 115 features a course thread and a friction ring between the top and bottom sub. Should the test string become stuck it is possible to back-off the upper assemblies at the safety joint by rotating anti-clockwise. The back-off torque required is 60% of the make-up torque. The hydraulic jar 116 combines a hydraulic time delay and mechanical trigger mechanism that delivers a controlled jarring action to help free stuck bottom hole assemblies. The hydraulic time delay provides a temporary resistance that allows the drill pipe to be stretched. The trigger mechanism causes the tubing stretch to be released, with the resulting sudden contraction delivering a substantial impact force.

Sample chamber 117 is mechanically connected to the hydraulic shut-in tool (HSIT) or Valve Assembly 118, allowing it to capture a fluid sample when the Valve Assembly closes. The Valve Assembly is the downhole tester valve that exposes the formation to the work string 122. It is operated by vertical motion. The tool is open when compressed and closed when extended. There is a metering mechanism on the tool that prevents it from being inadvertently opened, with compression having to be applied via the work string 122 for a certain time period before it will open. There is no time delay mechanism associated with tool closure. The recovery recorder carrier 119 contains a gauge that measures the hydrostatic pressure in the work string 122.

The impact reversing sub (IRS) 120 contains an internal brass pin that can be sheared by dropping a bar from surface down the work string 122. This then allows the higher pressure in the annulus 127 to enter the work string 122, allowing reverse circulation to occur. The pump out reversing sub (PORS) 121 is used as a backup to the IRS 120. In the event that the IRS 120 does not function, pressure is applied down the work string 122, causing a brass pin in the PORS to shear, allowing pressure communication between the work string 122 and annulus 127. Work string pressure is then bled off, with contents then reversed out by pump down the annulus 127. If blow-down operations are used to withdraw fluid from the test interval 128 into the work string 122 then the PORS is replaced with a multi cycle circulating valve (MCCV), which is indexed through several closed positions, a forward circulating position and a reverse circulating position, by cycling of pressure down the work string 122 between some threshold value above the pressure in the annulus 127 and another threshold value below the pressure in the annulus 127.

The resulting data can then be analyzed to provide the composition of gases and liquids at various depths and the amount of gases and liquids at various depths, and to precisely determine the originating depths of these gases and liquids. That analysis can include conversions of gas and liquid concentration to gas and liquid effective partial pressure using solubility law. It can include correction of compositional stoichiometries measured for difference in flow speed, for example when calculating the relative partial pressures of methane and ethane under kinetically-constrained conditions.

In another embodiment, it is possible to derives the same measurements and determine the same production factors without using the straddle packer assembly of FIG. 16. In this alternative embodiment, a variety of methods, including but not limited to swabbing, or fresh water circulation, can be employed to induce flow of fluids from all shale intervals penetrated by the well into the well. Properties of the produced fluid in the well as a function of depth can be determined using either a down hole spectroscopic analyzer deployed on a guide wire with electrical conductors, or a guide wire with a set of optical fibers connected to a spectroscopic analyzer situated at the surface. The spectroscopic analyzer is moved up and down across all the shale intervals to track changes in the produced fluid properties over time until the fluid column has reached a steady state or other condition, where this condition indicates that the fluid properties including composition, concentration and partial pressure can be related to the authentic reservoir in the formation.

A Method for Over-Saturated Gas Shale Reservoir Evaluation

In over-saturated shale intervals that also contain an appreciable amounts of hydrocarbon liquids, it may be desirable to determine the variation in concentration of each hydrocarbon species with depth. These data can be used to guide well trajectory in order to target specific locations within the shale or shale intervals with highest concentrations of these hydrocarbon liquids. In one case, these concentration versus depth logs can be obtained by first air drilling a well through the shale or shale intervals, then filling the well with water to a depth above the shale intervals, or to surface, and allowing the contacted shale intervals to flow gasses, salts and liquids into the wellbore. The disclosed method describes downhole analysis of the reservoir fluid using a solution gas sensor, i.e. a Raman spectrometer system including pressure, temperature, depth and conductivity sensors, in order to identify chemical composition and measure concentrations of hydrocarbon species solubilized at every depth in the wellbore water, and measure or determine changes in salinity and thus dissolved salt concentrations with depth. The wellbore fluid is traversed multiple times using the Raman spectrometer system, including pressure, temperature, depth and conductivity sensors, to then trend changes in hydrocarbon and salt concentration profiles, pressure profiles and temperature profiles through the wellbore fluid column over time. The established trends are then extrapolated backwards in time to the instant when water was first introduced into the well to determine the precise origins in the shale intervals for the production of particular hydrocarbon species. Measurement or estimation of factors, including temperature, pressure and salinity, that affect the solubility of a particular gas in the water can be used to convert such concentrations to accurate hydrocarbon effective partial pressures in the formation. For non-equilibrium conditions, formation effects on mass transport of different hydrocarbons can be estimated or measured in order to correct the measured wellbore concentrations for the composition and relative concentrations and partial pressures of the hydrocarbon in the formation. Increasing or decreasing the length of time allowed for shale intervals to flow gases, salts or liquids to the wellbore prior to measurement, or increasing or decreasing the hydraulic pressure at the formation before, during or after that time period, can also be performed in order to gain additional information about water and hydrocarbon mass transport through the formation.

In other cases, the analysis can be conducted using the Raman spectrometer as a chemical identifier to locate intervals in which certain desired hydrocarbons are present in greater amounts. This identification can occur when the Raman spectrometer produces a larger Raman scattering peak at a frequency or frequencies indicative of a particular hydrocarbon. It can occur when the Raman spectrometer produces a fluorescence emission peak indicative of a particular hydrocarbon. It can occur when the Raman spectrometer produces multiple Raman or fluorescence peaks indicative of a variety of hydrocarbons or other materials including dissolved salts or carbon dioxide. In some cases, the Raman spectrometer may indicate concentration of the gases, liquids or dissolved gases already in the wellbore or in samples collected from the wellbore. Analysis of hydrocarbon types, associated solubilized concentrations, salinity, pressure and temperature as a function of time, produced volume, source depth, and other factors provides indication of which shale interval and which vertical location within a shale interval provides the optimal hydrocarbon production target. This analysis can lead to calculation of estimated ultimate recovery factors for the hydrocarbons that are observed. This analysis can be conducted in a surface test mode on flowback fluid collected from a well or from a particular shale interval, either on discrete samples removed from the well or on the flowing fluid as it exits the wellbore. This analysis also can be conducted downhole on fluid or gases resident in the wellbore before, during or after completion of one or more shale intervals occurs. Wellbore treatments, such as adding acidified water, adding fresh water, adding hydrophilic solvents, or reducing or increasing wellbore pressure, may be undertaken before, during or after the analysis in order to enhance that analysis. Combination of the measurement modes with other fluid management equipment, such as straddle packers, in some cases enhances the analysis. Combination of the measurement results with other measurement results, such as core sample chemical analysis, in some cases enhances the analysis.

A Method for Under-Saturated Gas Shale Reservoir Evaluation

Under-saturated reservoirs by definition do not contain any free gas in the pore space, cleats or fracture network. As a result, pre-production analysis of gas occurrences requires analysis of the gas that is resident in the formation or in the fluid that the formation contains. The disclosed method describes chemical analysis of a shale interval using a Raman spectrometer. In one case, this analysis can be conducting using the Raman spectrometer as a solution gas sensor to measure gas concentrations. Measurement or estimation of factors, including temperature, pressure and salinity, that affect the solubility of a particular gas in that fluid then allow accurate calculation of the partial pressure of each gas in the fluid. Because those partial pressures can be measured under equilibrium conditions, they are highly accurate even in mixed gas systems. In other cases, the analysis can be conducted using the Raman spectrometer as a chemical identifier to locate intervals in which certain desired hydrocarbons are present in greater amounts. This identification can occur when the Raman spectrometer produces a larger Raman scattering peak at a frequency or frequencies indicative of a particular hydrocarbon. It can occur when the Raman spectrometer produces a fluorescence emission peak indicative of a particular hydrocarbon. It can occur when the Raman spectrometer produces multiple Raman or fluorescence peaks indicative of a variety of hydrocarbons or other materials including dissolved salts or carbon dioxide. In some cases, the Raman spectrometer may indicate concentration of the gases, liquids or dissolved gases in the wellbore or in samples collected from the wellbore. It may indicate the presence of gases, liquids or dissolved gases in the wellbore or in samples collected or produced from the wellbore. It may indicate other factors, including but not limited to fluid type, fluid salinity, temperature, or dissolved salt concentrations. Analysis of such data as a function of time, produced volume, source depth, and other factors provides indication of which shale interval and which lateral location within a shale interval provides the optimal hydrocarbon production target. This analysis can lead to calculation of estimated ultimate recovery factors for the hydrocarbons that are observed. This analysis can be conducted in a surface test mode on flowback fluid collected from a well or from a particular shale interval, either on discrete samples removed from the well or on the flowing fluid as it exits the wellbore. This analysis also can be conducted downhole on fluid or gases resident in the wellbore before, during or after completion of one or more shale intervals occurs. Wellbore treatments, such as adding acidified water, adding fresh water, adding hydrophilic solvents, or reducing or increasing wellbore pressure, may be undertaken before, during or after the analysis in order to enhance that analysis. Combination of the measurement modes with other sensors, such as pressure and conductivity sensors, or with other fluid management equipment, such as straddle packers, in some cases enhances the analysis. Combination of the measurement results with other measurement results, such as core sample chemical analysis, in some cases enhances the analysis.

In some cases, background signals such as fluorescence can obscure the Raman signals from the gases in a particular fluid. Various methods can be undertaken to minimize such background signals, including adjusting the Raman excitation frequency so that fluorescence is minimized.

A Method for Oil Shale Reservoir Evaluation

In oil shales it may be desirable to determine the variation in chemical composition and also concentration of solubilized gases. These data can be used to determine gas-oil ratio, and origin of any waxes, paraffins, or ashphaltenes and so guide well trajectory in order to target specific locations within the shale or shales with highest concentrations of preferred lighter oils. These composition and concentration versus depth logs can be obtained by logging across all contributing shale intervals. The disclosed method describes downhole analysis of the formation fluid using a chemical sensor, i.e. a Raman spectrometer system, including pressure, temperature, depth and conductivity sensors, to measure hydrocarbon composition and concentrations in the wellbore. Measurement or estimation of factors, including temperature, pressure and salinity and gas-oil ratio can be used to pin-point sources of solubilized gases, waxes, parafins and asphaltenes. The disclosed method describes chemical analysis of a shale interval using a Raman spectrometer. In one case, this analysis can be conducting using the Raman spectrometer as a sensor to measure dissolved hydrocarbon concentrations. Measurement or estimation of factors, including temperature, pressure and salinity, that affect the solubility of a particular gas in that fluid then allow accurate calculation of the partial pressure of each hydrocarbon in the fluid. Because those partial pressures can be measured under equilibrium conditions, they are highly accurate even in mixed hydrocarbon systems. In other cases, the analysis can be conducted using the Raman spectrometer as a chemical identifier to locate intervals in which certain desired hydrocarbons are present in greater amounts. This identification can occur when the Raman spectrometer produces a larger Raman scattering peak at a frequency or frequencies indicative of a particular hydrocarbon. It can occur when the Raman spectrometer produces a fluorescence emission peak indicative of a particular hydrocarbon. It can occur when the Raman spectrometer produces multiple Raman or fluorescence peaks indicative of a variety of hydrocarbons or other materials including dissolved salts or carbon dioxide. In some cases, the Raman spectrometer may indicate concentration of the gases, liquids or dissolved gases in the wellbore or in samples collected from the wellbore. It may indicate the presence of gases, liquids or dissolved gases in the wellbore or in samples collected or produced from the wellbore. It may indicate other factors, including but not limited to fluid type, fluid salinity, temperature, or dissolved salt concentrations. Analysis of such data as a function of time, produced volume, source depth, and other factors provides indication of which shale interval and which lateral location within a shale interval provides the optimal hydrocarbon production target. This analysis can lead to calculation of estimated ultimate recovery factors for the hydrocarbons that are observed. This analysis can be conducted in a surface test mode on flowback fluid collected from a well or from a particular shale interval, either on discrete samples removed from the well or on the flowing fluid as it exits the wellbore. This analysis also can be conducted downhole on fluid or gases resident in the wellbore before, during or after completion of one or more shale intervals occurs. Wellbore treatments, such as adding acidified water, adding fresh water, adding hydrophilic solvents, or reducing or increasing wellbore pressure, may be undertaken before, during or after the analysis in order to enhance that analysis. Combination of the measurement modes with other sensors, such as pressure and conductivity sensors, or with other fluid management equipment, such as straddle packers, in some cases enhances the analysis. Combination of the measurement results with other measurement results, such as core sample chemical analysis, in some cases enhances the analysis.

In some cases, background signals such as fluorescence can obscure the Raman signals from the gases in a particular fluid. Various methods can be undertaken to minimize such background signals, including adjusting the Raman excitation frequency so that fluorescence is minimized.

Example 1

A shale gas well is completed and produced such that fluids from the shale interval pass through the wellbore to the pump through the tubing and out of the wellhead. Production of fluids is stopped and pump and tubing are removed from the wellbore. A Raman spectrometer, or its probe connected to the Raman spectrometer via an optical fiber, is lowered into the wellbore and a log of the concentration of gases, especially methane and ethane, in the wellbore fluid as a function of depth is collected. The gas concentrations are converted to gas partial pressures by using standard solubility law. As a result, the partial pressures of the various gases as a function of depth are obtained. Those partial pressures are used to calculate estimated ultimate recovery of the hydrocarbons identified. Alternately, the Raman signals measured are not converted to concentrations or partial pressures. Instead, a normalized hydrocarbon peak area or peak height that they contain is used to indicate depths containing higher levels of a desirable hydrocarbon when compared to other depths or lateral locations in the same shale interval as intersected by other wells.

Example 2

A shale gas well is drilled but not completed. The drilling fluids residual in the wellbore are removed in order to instigate additional fluid from the shale interval into the wellbore. A Raman spectrometer, or its probe connected to the Raman spectrometer via an optical fiber, is lowered into the wellbore and a log of the concentration of gases, especially methane and ethane, in the wellbore fluid as a function of depth is collected. The measured gas concentrations are converted to gas partial pressures by using standard solubility law. As a result, the partial pressures of the various gases as a function of depth are obtained. Those partial pressures are used to calculate estimated ultimate recovery of the hydrocarbons identified. Alternately, the Raman signals measured are not converted to concentrations or partial pressures. Instead, a normalized hydrocarbon peak area or peak height that they contain is used to indicate depths containing higher levels of a desirable hydrocarbon when compared to other depths or lateral locations in the same shale interval as intersected by other wells.

Example 3

A shale gas well is drilled but not completed. The drilling fluids residual in the wellbore are left in place for a certain amount of time in order to allow them to reach chemical equilibrium with fluids in the surrounding shale interval. A Raman spectrometer, or its probe connected to the Raman spectrometer via an optical fiber, is lowered into the wellbore and a log of the concentration of gases, especially methane and ethane, in the wellbore fluid as a function of depth is collected. The measured gas concentrations are converted to gas partial pressures by using standard solubility law. As a result, the partial pressures of the various gases as a function of depth are obtained. Those partial pressures are used to calculate estimated ultimate recovery of the hydrocarbons identified. Alternately, the Raman signals measured are not converted to concentrations or partial pressures. Instead, a normalized hydrocarbon peak area or peak height that they contain is used to indicate depths containing higher levels of a desirable hydrocarbon when compared to other depths or lateral locations in the same shale interval as intersected by other wells.

Example 4

A shale gas well is drilled but not completed. A straddle packer or other zonal isolation system, as depicted in FIG. 2, is lowered into the wellbore to a depth corresponding to a zone of interest, the zonal isolation system is actuated and the zone of interest is thereby isolated from the rest of the wellbore. Any fluids residual in the drill string or rods above the zonal isolation system are removed in order to instigate additional fluid from the zone of interest into the drill string or rods. Alternately, the zonal isolation system includes a pump that is used to remove fluid from the wellbore immediately in front of the zone of interest in order to instigate additional fluid flow from that zone. In both cases, the zonal isolation system prevents production of fluids from other zones into the drill string or rods. A Raman spectrometer, or its probe connected to the Raman spectrometer via an optical fiber, is lowered into the drill string or rods and a log of the concentration of gases, especially methane and ethane, in the wellbore fluid as a function of depth is collected. The measured gas concentrations are converted to gas partial pressures by using standard solubility law. As a result, the partial pressures of the various gases is the zone of interest are obtained. Those partial pressures are used to calculate estimated ultimate recovery of the hydrocarbons identified. Alternately, the Raman signals measured are not converted to concentrations or partial pressures. Instead, a normalized hydrocarbon peak area or peak height that they contain is used to indicate depths containing higher levels of a desirable hydrocarbon when compared to other depths or lateral locations in the same shale interval as intersected by other wells.

Example 5

A shale gas well is drilled with air but not completed. Fresh source water is added to the wellbore and is left in place for a period of time up to a certain depth above all exposed shale intervals. A Raman spectrometer, or its probe connected to the Raman spectrometer via an optical fiber, is lowered into the wellbore and a log of the concentration of produced gases, especially methane, ethane and higher hydrocarbon gasses, as a function of depth is collected. Concurrently, logs as a function of depth of temperature, pressure, conductivity, and pH are collected. These logs are repeated to trend the change in depths of transitions between the different gas and liquid hydrocarbon species in the fluid column over time. The precise origin of these different hydrocarbons within the shale intervals is determined by extrapolating these trends back in time to the instant when fresh water was first introduced in the well. Depths at which high levels and low levels of produced hydrocarbons are entering the wellbore are noted as high and low priority production targets, respectively. Stationary measurements are also conducted at depths of particular interest. Both stationary and moving measurements can be repeated over time in order to evaluate any temporal changes in the observed hydrocarbon or saline fluid flux to the wellbore. In the case of evolution of gas phase hydrocarbons from certain intervals, the concentration measurements can be performed over longer or shorter spectrometer exposure times in order to integrate over multiple gas bubbles and estimate effective hydrocarbon flux to the wellbore. Similarly, Rayleigh scattering at the bubble-water interface can be assessed by measuring the shot noise levels and laser line peak size in the spectrometer and thereby size and number of bubbles can be estimated, in some cases. Combination of bubble size and count estimates with formation pressure measurements can provide estimates of hydrocarbon flux to the wellbore.

In some cases, the measurement results enable identification of intervals of relatively higher and lower production value, although it may not be possible to calculate accurate, independent gas composition, gas partial pressures, gas in place and estimated ultimate recovery factors (where gas in this case can include methane, ethane and higher order hydrocarbons).

In other cases, these measurements can also allow the location of highest concentrations of methane, ethane and higher hydrocarbon gases to be precisely determined. By accurately determining the kinetic relationship between the concentrations of methane, ethane, and higher hydrocarbons, the effective partial pressure of those constituents can be calculated and the gas-in-place and estimated ultimate recovery of those constituents can be calculated—in some cases using relationships developed to account for kinetic mass transport relationships between the wellbore and the formation. In this example, circulating fresh water into the well is presumed to disturb the thermodynamic equilibrium between the adsorbed state and free state of each gas and liquids, resulting in some of the gas and liquids in the adsorbed state transferring to the free state. It may also change the effective permeability of the formation. This reduction in ratio of adsorbed gas to free gas and liquids results in an increase in equilibrium partial pressure of both states, and forcing mass transport of the gases and liquids to relieve that increased pressure.

In cases where initial hydrocarbon flux to the wellbore is more rapid than can be practically measured by the Raman spectrometer, or in cases where isolation and treatment of specific shale intervals is desired, individual intervals can be isolated using physical isolation methods such as straddle packers, and the same measurements can be performed in the rods above the test valve.

Example 6

A shale gas well is drilled with air but not completed. A particular interval is isolated from other intervals using a physical isolation method such as a straddle packer assembly. Fresh source water is added to the rods above the straddle packer assembly and the test valve is opened so that the water flows down to the interval and contacts the shale. Free gas and hydrocarbon liquids begin to enter the test string. As those gases and liquids travel up the test string to the wellhead, a pressure increase is observed to occur at the wellhead. Alternately, or in addition, the gas and liquids are diverted into a surface manifold or other sample holder and analyzed at the wellhead or in a laboratory in order to evaluate composition of hydrocarbons and concentration of hydrocarbons. The resulting data is noted and then the process is repeated for an interval of a different depth. By comparing the data results at different depths, intervals of higher and lower production value are identified.

In each case, the partial pressures of gases that may be present may be used to identify depths at which desirable gas(es) occur, and therefore guide completion and production activities. In addition, those partial pressures can be used to calculate the gas content and gas-in-place for each type of gas. In addition, measurement of non-hydrocarbon gases such as carbon dioxide and nitrogen can further be used to guide completion and production activities.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

This specification is to be construed as illustrative only and is for the purpose of teaching those skilled in the art the manner of carrying out the disclosure. It is to be understood that the forms of the disclosure herein shown and described are to be taken as the presently preferred embodiments. As already stated, various changes may be made in the shape, size and arrangement of components or adjustments made in the steps of the method without departing from the scope of this invention. For example, equivalent elements may be substituted for those illustrated and described herein and certain features of the invention maybe utilized independently of the use of other features, all as would be apparent to one skilled in the art after having the benefit of this description of the invention.

While specific embodiments have been illustrated and described, numerous modifications are possible without departing from the spirit of the disclosure, and the scope of protection is only limited by the scope of the accompanying claims.

What we claim is:

1. A method comprising:
   intersecting an under-saturated shale interval of a shale reservoir with a wellbore;
   stimulating the under-saturated shale interval to produce gas, wherein the produced gas solubilizes within wellbore fluid within the wellbore to form solubilized gas;
   lowering a solution gas sensor down the wellbore;
   testing wellbore fluid within the wellbore intersecting the shale interval for the presence of the solubilized gas using the solution gas sensor, wherein the testing using the solution gas sensor forms a signal;
   identifying a chemical composition of the solubilized gas using the signal, and determining an absorbed gas content in the under-saturated shale interval of the shale reservoir by determining a partial pressure of the solubilized gas within the wellbore fluid using the signal.

2. The method of claim 1, wherein determining the partial pressure of the solubilized gas within the wellbore fluid using the signal comprises:
   determining a concentration of the solubilized gas within the wellbore fluid using the signal; and
   correlating the concentration of the solubilized gas to partial pressure of the solubilized gas within the wellbore fluid.

3. The method of claim 2, wherein determining the absorbed gas content in the shale interval of the under-saturated shale reservoir using the partial pressure of the solubilized gas within the wellbore fluid comprises:

correlating the partial pressure of the solubilized gas within the wellbore fluid to a partial pressure of the gas within the under-saturated shale interval of the shale reservoir; and correlating the partial pressure of the gas within the under-saturated shale interval of the shale reservoir to the absorbed gas content in the under-saturated shale interval of the shale reservoir.

4. The method of claim 2, wherein the concentration of the solubilized gas within the wellbore fluid is determined versus depth using the signal.

5. The method of claim 1, wherein the partial pressure of the solubilized gas within the wellbore fluid is determined versus depth using the signal.

6. The method of claim 1, wherein the wellbore only intersects one under-saturated shale interval of the shale reservoir.

7. The method of claim 1, further comprising, prior to testing wellbore fluid, isolating the under-saturated shale interval.

8. The method of claim 7, wherein the under-saturated shale interval is isolated using bridge plugs or straddle packers.

9. The method of claim 1, wherein the solubilized gas comprises methane.

10. The method of claim 1, wherein the solubilized gas comprises carbon dioxide.

11. The method of claim 1, wherein the solubilized gas comprises propane.

12. The method of claim 1, wherein the solution gas sensor comprises a concentration sensor.

13. The method of claim 1, wherein the solution gas sensor comprises a pressure sensor.

14. The method of claim 1, wherein the solution gas sensor comprises an optical spectrometer.

15. The method of claim 1, wherein the solution gas sensor comprises a Raman spectrometer.

16. The method of claim 1, wherein the solution gas sensor comprises a Raman spectrometer, a pressure sensor, a temperature sensor, a depth sensor, and a conductivity sensor.

17. The method of claim 1, wherein the under-saturated shale interval comprises inorganic sedimentary rock containing kerogen.

18. The method of claim 1, wherein stimulating the under-saturated shale interval to produce gas comprises fracturing the under-saturated shale interval.

19. The method of claim 1, wherein stimulating the under-saturated shale interval to produce gas comprises: adding acidified water to the wellbore, adding water to the wellbore, adding hydrophilic solvent to the wellbore, or increasing wellbore pressure.

20. A method comprising:
intersecting an over-saturated shale interval of a shale reservoir with a wellbore;
stimulating the over-saturated shale interval to produce gas, wherein the produced gas solubilizes within wellbore fluid within the wellbore to form solubilized gas;
lowering a solution gas sensor down the wellbore;
testing wellbore fluid within the wellbore intersecting the over-saturated shale interval for the presence of the solubilized gas using the solution gas sensor, wherein the testing using the solution gas sensor forms a signal;
identifying a chemical composition of the solubilized gas using the signal; and
determining an absorbed gas content in the under-saturated shale interval of the shale reservoir by determining a partial pressure of the solubilized gas within the wellbore fluid using the signal.

21. The method of claim 20, wherein the wellbore only intersects one over-saturated shale interval of the shale reservoir.

22. The method of claim 20, further comprising, prior to testing wellbore fluid, isolating the over-saturated shale interval.

23. The method of claim 22, wherein the over-saturated shale interval is isolated using bridge plugs or straddle packers.

24. The method of claim 20, wherein the solubilized gas comprises methane, carbon dioxide, or propane.

25. The method of claim 20, wherein the solution gas sensor comprises a concentration sensor.

26. The method of claim 20, wherein the solution gas sensor comprises a pressure sensor.

27. The method of claim 20, wherein the solution gas sensor comprises an optical spectrometer.

28. The method of claim 20, wherein the solution gas sensor comprises a Raman spectrometer.

29. The method of claim 20, wherein the solution gas sensor comprises a Raman spectrometer, a pressure sensor, a temperature sensor, a depth sensor, and a conductivity sensor.

30. The method of claim 20, wherein the over-saturated shale interval comprises inorganic sedimentary rock containing kerogen.

31. The method of claim 20, wherein stimulating the over-saturated shale interval to produce gas comprises fracturing the over-saturated shale interval.

32. The method of claim 20, wherein stimulating the over-saturated shale interval to produce gas comprises: adding acidified water to the wellbore, adding water to the wellbore, adding hydrophilic solvent to the wellbore, or increasing wellbore pressure.

* * * * *